(12) United States Patent
Smith, III et al.

(10) Patent No.: US 10,335,351 B2
(45) Date of Patent: Jul. 2, 2019

(54) PERSONAL CARE ARTICLES AND METHODS

(71) Applicant: The Procter & Gamble Company, Cincinnati, OH (US)

(72) Inventors: Edward Dewey Smith, III, Mason, OH (US); Shawn David McConaughy, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/429,225

(22) Filed: Feb. 10, 2017

(65) Prior Publication Data

US 2017/0151132 A1    Jun. 1, 2017

Related U.S. Application Data

(63) Continuation of application No. 13/438,918, filed on Apr. 4, 2012, now Pat. No. 9,592,181.

(60) Provisional application No. 61/471,628, filed on Apr. 4, 2011, provisional application No. 61/523,824, filed on Aug. 15, 2011.

(51) Int. Cl.

| | |
|---|---|
| *A47K 7/02* | (2006.01) |
| *A61K 8/02* | (2006.01) |
| *A61Q 5/02* | (2006.01) |
| *A61Q 9/02* | (2006.01) |
| *A61Q 19/00* | (2006.01) |
| *A61Q 19/10* | (2006.01) |
| *A47K 7/03* | (2006.01) |
| *A61K 8/26* | (2006.01) |
| *A61K 8/27* | (2006.01) |

(Continued)

(52) U.S. Cl.
CPC .............. *A61K 8/0208* (2013.01); *A47K 7/03* (2013.01); *A61K 8/26* (2013.01); *A61K 8/27* (2013.01); *A61K 8/463* (2013.01); *A61K 8/466* (2013.01); *A61K 8/4933* (2013.01); *A61Q 5/02* (2013.01); *A61Q 9/02* (2013.01); *A61Q 19/002* (2013.01); *A61Q 19/10* (2013.01); *A61K 2800/74* (2013.01); *A61K 2800/87* (2013.01)

(58) Field of Classification Search
CPC .... A61K 8/0208; A61K 8/466; A61K 8/4933; A61K 8/463; A61K 8/26; A61K 7/03; A61K 2800/74; A61K 2800/87; A61Q 5/02; A61Q 19/10
See application file for complete search history.

(56) References Cited

U.S. PATENT DOCUMENTS

| | | |
|---|---|---|
| 2,438,091 A | 3/1948 | Lynch |
| 2,528,378 A | 10/1950 | Mannheimer |

(Continued)

FOREIGN PATENT DOCUMENTS

| | | |
|---|---|---|
| CN | 1046273 | 10/1990 |
| CN | 1117835 | 3/1996 |

(Continued)

OTHER PUBLICATIONS

U.S. Appl. No. 15/877,490, dated Jan. 23, 2018, McConaughy et al.

(Continued)

*Primary Examiner* — Jennifer C Chiang

(57) ABSTRACT

A personal care article can include a composition and a substrate. The article can be compliant to a surface.

19 Claims, 3 Drawing Sheets

(51) Int. Cl.
    *A61K 8/46*    (2006.01)
    *A61K 8/49*    (2006.01)

(56)    References Cited

U.S. PATENT DOCUMENTS

| | | |
|---|---|---|
| 2,658,072 A | 11/1953 | Kosmin |
| 3,689,437 A | 9/1972 | McLaughlin |
| 3,949,137 A | 4/1976 | Akrongold |
| 4,181,632 A | 1/1980 | Schebece |
| 4,190,550 A | 2/1980 | Campbell |
| 4,207,198 A | 6/1980 | Kenkare |
| 4,328,131 A | 5/1982 | Carson, Jr. et al. |
| 4,335,025 A | 6/1982 | Barker et al. |
| 4,367,999 A | 1/1983 | Benuzzi |
| 4,510,641 A | 4/1985 | Morris |
| 4,515,703 A | 5/1985 | Haq |
| 4,554,097 A | 11/1985 | Schebece et al. |
| 4,603,069 A | 7/1986 | Haq et al. |
| 4,654,158 A | 3/1987 | Shepherd |
| 4,665,580 A | 5/1987 | Morris |
| 4,735,739 A | 4/1988 | Floyd et al. |
| 4,812,253 A | 3/1989 | Small et al. |
| 4,861,508 A | 8/1989 | Wegener et al. |
| 4,935,158 A | 6/1990 | Aszman et al. |
| 4,953,250 A | 9/1990 | Brown |
| 4,987,632 A | 1/1991 | Rowe et al. |
| 5,066,494 A | 11/1991 | Becher |
| 5,108,642 A | 4/1992 | Aszman et al. |
| 5,132,115 A | 7/1992 | Wolter et al. |
| 5,139,705 A | 8/1992 | Wittpenn, Jr. et al. |
| 5,225,097 A | 7/1993 | Kacher et al. |
| 5,227,086 A | 7/1993 | Kacher et al. |
| 5,262,079 A | 11/1993 | Kacher et al. |
| 5,264,144 A | 11/1993 | Moroney et al. |
| 5,264,145 A | 11/1993 | French et al. |
| 5,308,180 A | 5/1994 | Pournoor et al. |
| 5,312,559 A | 5/1994 | Kacher et al. |
| RE34,692 E | 8/1994 | Becher |
| 5,340,492 A | 8/1994 | Kacher et al. |
| 5,387,362 A | 2/1995 | Tollens et al. |
| 5,393,466 A | 2/1995 | Ilardi et al. |
| 5,433,883 A | 7/1995 | Massaro et al. |
| 5,433,894 A | 7/1995 | Massaro et al. |
| 5,482,643 A | 1/1996 | Chambers et al. |
| 5,487,884 A | 1/1996 | Bissett et al. |
| 5,520,840 A | 5/1996 | Massaro et al. |
| 5,523,017 A | 6/1996 | Moran et al. |
| 5,540,854 A | 7/1996 | Fair et al. |
| 5,652,228 A | 7/1997 | Bissett |
| 5,681,852 A | 10/1997 | Bissett |
| 5,683,971 A | 11/1997 | Rose et al. |
| 5,683,973 A | 11/1997 | Post et al. |
| 5,698,475 A | 12/1997 | Vlasblom |
| 5,702,992 A | 12/1997 | Martin et al. |
| 5,703,025 A | 12/1997 | Zyngier et al. |
| 5,704,723 A | 1/1998 | Salisian |
| 5,756,438 A | 5/1998 | Rau et al. |
| 5,786,311 A | 7/1998 | Zyngier et al. |
| 5,824,296 A | 10/1998 | Dubief et al. |
| 5,888,953 A | 3/1999 | Harris et al. |
| 5,916,856 A | 6/1999 | Massaro et al. |
| 5,985,808 A | 9/1999 | He et al. |
| 5,968,852 A | 10/1999 | Vlasblom |
| 5,972,860 A | 10/1999 | Eshita et al. |
| 6,026,534 A | 2/2000 | Gonda et al. |
| 6,028,042 A | 2/2000 | Chambers et al. |
| 6,063,390 A | 5/2000 | Farrell et al. |
| 6,074,997 A | 6/2000 | Rau et al. |
| 6,153,208 A | 11/2000 | McAtee et al. |
| 6,162,457 A | 12/2000 | Martz |
| 6,206,863 B1 | 3/2001 | Skewes et al. |
| 6,217,854 B1 | 4/2001 | Farrell et al. |
| 6,245,343 B1 | 6/2001 | Roulier et al. |
| 6,322,801 B1 | 11/2001 | Lorenzi et al. |
| 6,328,811 B1 | 12/2001 | Martin et al. |
| 6,376,046 B1 | 4/2002 | Hoshino et al. |
| 6,391,835 B1 | 5/2002 | Gott et al. |
| 6,395,691 B1 | 5/2002 | Tsaur |
| 6,428,799 B1 | 8/2002 | Cen et al. |
| 6,467,981 B1 | 10/2002 | Gueret |
| 6,491,928 B1 * | 12/2002 | Smith, III .............. A61F 13/36 424/401 |
| 6,491,933 B2 | 12/2002 | Lorenzi et al. |
| 6,491,937 B1 | 12/2002 | Slavtcheff et al. |
| 6,547,468 B2 * | 4/2003 | Gruenbacher ........... A47K 7/03 401/132 |
| 6,550,092 B1 | 4/2003 | Brown et al. |
| 6,607,739 B1 | 8/2003 | Wallo |
| 6,638,527 B2 | 10/2003 | Gott et al. |
| 6,638,611 B2 | 10/2003 | Seth |
| 6,645,611 B2 | 11/2003 | Seth |
| 6,677,294 B2 | 1/2004 | Shaw et al. |
| 6,730,317 B2 | 5/2004 | Gueret |
| 6,753,063 B1 | 6/2004 | Pung et al. |
| 6,783,294 B2 | 8/2004 | Duden et al. |
| 6,835,701 B2 | 12/2004 | Seipel et al. |
| 6,867,380 B2 | 3/2005 | Miki et al. |
| 6,883,353 B2 | 4/2005 | Goldoni et al. |
| 6,878,380 B2 | 5/2005 | Farrell et al. |
| 6,902,338 B2 | 6/2005 | Puvvada et al. |
| 6,903,057 B1 | 6/2005 | Tsaur |
| 6,977,238 B1 | 12/2005 | Wetzel et al. |
| 6,992,054 B2 | 1/2006 | Lee et al. |
| 7,033,064 B2 | 4/2006 | Gillette |
| 7,033,964 B2 | 4/2006 | Gillette |
| 7,101,612 B2 | 9/2006 | Lang et al. |
| 7,115,535 B1 | 10/2006 | Smith, III et al. |
| 7,115,551 B2 | 10/2006 | Hasenoehrl et al. |
| 7,229,956 B2 | 6/2007 | Bedford et al. |
| 7,276,459 B1 | 10/2007 | Lang et al. |
| 7,288,513 B2 | 10/2007 | Taylor et al. |
| 7,320,953 B2 | 1/2008 | Grissett et al. |
| 7,335,626 B2 | 2/2008 | Keenan et al. |
| 7,345,014 B2 | 3/2008 | Keenan et al. |
| 7,348,299 B2 | 3/2008 | Keenan et al. |
| 7,381,692 B2 | 6/2008 | Grissett et al. |
| 7,381,693 B2 | 6/2008 | Kennan et al. |
| 7,419,321 B2 | 9/2008 | Tereschouk |
| 7,452,547 B2 | 11/2008 | Lambino et al. |
| 7,462,348 B2 | 12/2008 | Gruenbacher et al. |
| 7,514,071 B2 | 4/2009 | Simon et al. |
| 7,581,273 B2 | 9/2009 | Dobrin et al. |
| 7,584,519 B2 | 9/2009 | Ouellette et al. |
| 7,651,290 B2 | 1/2010 | Bauer et al. |
| 7,674,058 B2 | 3/2010 | Berger Sharp et al. |
| 7,846,462 B2 | 12/2010 | Spadini et al. |
| 7,874,756 B2 | 1/2011 | Nuebel et al. |
| 8,147,853 B2 | 4/2012 | Taylor et al. |
| 8,157,464 B2 | 4/2012 | Prax |
| 8,308,388 B2 | 11/2012 | Guay |
| 8,357,383 B2 | 1/2013 | Spadini et al. |
| 8,475,817 B2 | 7/2013 | Hasenoehrl et al. |
| 8,534,947 B2 | 9/2013 | Prax |
| 9,554,978 B2 | 1/2017 | McConaughy et al. |
| 9,907,738 B2 | 3/2018 | McConaughy et al. |
| 2001/0003565 A1 | 6/2001 | Mcosker et al. |
| 2001/0028894 A1 | 10/2001 | Gueret |
| 2002/0178507 A1 | 12/2002 | Goldoni et al. |
| 2002/0192268 A1 | 12/2002 | Alwattari et al. |
| 2003/0079323 A1 | 5/2003 | Ngai |
| 2003/0140439 A1 | 7/2003 | Durden et al. |
| 2003/0143263 A1 | 7/2003 | Durden et al. |
| 2003/0180242 A1 | 9/2003 | Eccard et al. |
| 2003/0194425 A1 | 10/2003 | Simon et al. |
| 2003/0203010 A1 | 10/2003 | Wallo |
| 2003/0228352 A1 | 12/2003 | Hasenoehrl et al. |
| 2004/0116017 A1 | 6/2004 | Smith, III et al. |
| 2004/0147189 A1 | 7/2004 | Smith, III et al. |
| 2004/0170670 A1 | 9/2004 | Smith et al. |
| 2004/0175343 A1 | 9/2004 | Osborne et al. |
| 2004/0176002 A1 | 9/2004 | Siegwart |
| 2004/0237234 A1 | 12/2004 | Young et al. |
| 2004/0237235 A1 | 12/2004 | Visioli et al. |
| 2005/0148260 A1 | 7/2005 | Kopacz et al. |

(56) References Cited

U.S. PATENT DOCUMENTS

| | | |
|---|---|---|
| 2005/0202068 A1 | 9/2005 | Hasenoehrl et al. |
| 2005/0276827 A1 | 12/2005 | Macedo et al. |
| 2005/0276828 A1 | 12/2005 | Grissett et al. |
| 2006/0097170 A1 | 5/2006 | Prinz et al. |
| 2006/0135026 A1 | 6/2006 | Arendt et al. |
| 2006/0141014 A1 | 6/2006 | Eknoian et al. |
| 2006/0246119 A1 | 11/2006 | Eknoian et al. |
| 2007/0048359 A1 | 3/2007 | Bolton |
| 2007/0071797 A1 | 3/2007 | Hernandez-Munoa et al. |
| 2007/0099813 A1 | 5/2007 | Luizzi et al. |
| 2007/0130706 A1 | 6/2007 | Buhrow et al. |
| 2007/0130707 A1 | 6/2007 | Cohen et al. |
| 2007/0219515 A1* | 9/2007 | Marsh ................ A61F 13/8405 604/359 |
| 2007/0283516 A1 | 12/2007 | Rasmussen et al. |
| 2008/0104787 A1 | 5/2008 | Keenan et al. |
| 2008/0116096 A1 | 5/2008 | Johnson et al. |
| 2008/0145388 A1 | 6/2008 | Roreger et al. |
| 2008/0168748 A1 | 7/2008 | McCloskey |
| 2008/0247806 A1 | 10/2008 | Todd et al. |
| 2008/0299269 A1 | 12/2008 | Mane et al. |
| 2009/0028808 A1 | 1/2009 | Cetti et al. |
| 2009/0178692 A1 | 7/2009 | Warr et al. |
| 2009/0246376 A1 | 10/2009 | Gunn et al. |
| 2009/0324520 A1 | 12/2009 | Cetti et al. |
| 2010/0130988 A1 | 5/2010 | Bolton |
| 2011/0278429 A1 | 11/2011 | Jha et al. |
| 2011/0290904 A1 | 12/2011 | Mane et al. |
| 2012/0028869 A1 | 2/2012 | Crawford et al. |
| 2012/0246851 A1 | 10/2012 | Smith, III et al. |
| 2012/0246852 A1 | 10/2012 | Smith, III et al. |
| 2012/0252715 A1 | 10/2012 | McConaughy et al. |
| 2013/0043145 A1 | 2/2013 | Smith, III et al. |
| 2013/0043146 A1 | 2/2013 | Smith, III et al. |
| 2013/0043147 A1 | 2/2013 | Smith, III et al. |
| 2013/0118518 A1 | 5/2013 | Spadini et al. |
| 2013/0266622 A1 | 10/2013 | Mcconaughy et al. |
| 2015/0000058 A1 | 1/2015 | McConaughy et al. |
| 2017/0096625 A1 | 4/2017 | McConaughy et al. |

FOREIGN PATENT DOCUMENTS

| | | |
|---|---|---|
| CN | 1318622 | 10/2001 |
| DE | 19744213 | 4/1999 |
| DE | 20017205 | 12/2000 |
| DE | 20304298 | 6/2003 |
| DE | 10301838 | 7/2004 |
| DE | 202004007851 | 8/2004 |
| EP | 0032793 B1 | 3/1984 |
| EP | 0047116 B1 | 7/1985 |
| EP | 0161911 | 11/1985 |
| EP | 0211664 | 2/1987 |
| EP | 0272492 A2 | 6/1988 |
| EP | 0353013 | 1/1990 |
| EP | 387693 | 9/1990 |
| EP | 387694 | 9/1990 |
| EP | 0863201 A2 | 9/1998 |
| EP | 1000605 A2 | 5/2000 |
| EP | 1106165 | 6/2001 |
| EP | 1153554 A1 | 11/2001 |
| EP | 2105061 | 9/2009 |
| FR | 1190521 | 10/1959 |
| FR | 2822045 | 9/2002 |
| FR | 2855741 | 12/2004 |
| GB | 2163947 A | 3/1986 |
| GB | 2222526 A | 3/1990 |
| JP | 61277608 A2 | 12/1986 |
| JP | 02265516 | 10/1990 |
| JP | 08084684 | 4/1996 |
| JP | 09299271 | 11/1997 |
| JP | 10000170 | 1/1998 |
| JP | 10183194 A1 | 7/1998 |
| JP | 2002142857 | 5/2002 |
| JP | 2002275031 | 9/2002 |
| JP | 2002315689 | 10/2002 |
| JP | 2004016560 | 1/2004 |
| JP | 2004236996 | 8/2004 |
| JP | 2006082263 | 3/2006 |
| JP | 2006130194 | 5/2006 |
| JP | 2009292750 | 12/2009 |
| JP | 2010046129 | 3/2010 |
| SE | 8703015 | 2/1989 |
| WO | 95/00116 | 1/1995 |
| WO | 95/11887 | 5/1995 |
| WO | 95/26710 A1 | 10/1995 |
| WO | 1996/631187 A2 | 3/1996 |
| WO | 96/31187 A2 | 10/1996 |
| WO | 97/04683 | 2/1997 |
| WO | 98/27193 A1 | 6/1998 |
| WO | 98/28399 A1 | 7/1998 |
| WO | 2009/828399 A1 | 7/1998 |
| WO | 99/31184 | 6/1999 |
| WO | 01/08655 A1 | 2/2001 |
| WO | 01/08658 A1 | 2/2001 |
| WO | 03/053397 A1 | 7/2003 |
| WO | 2006/036976 | 4/2006 |
| WO | 2008/113973 A1 | 9/2008 |

OTHER PUBLICATIONS

U.S. Appl. No. 29/459,273, dated Jun. 27, 2013, Althaus.
U.S. Appl. No. 29/459,274, dated Jun. 27, 2013, Althaus.
PCT International Search Report and Written Opinion for PCT/US2012/032054 dated Jul. 4, 2012.
PCT International Search Report and Written Opinion for PCT/US2012/032111 dated Dec. 17, 2012.
International Search Report and Written Opinion of PCT/US00/01387 dated Sep. 20, 2000.
International Search Report and Written Opinion of PCT/US2012/050873 dated Dec. 10, 2012.
International Search Report and Written Opinion of PCT/US2012/050874 dated Dec. 12, 2012.
International Search Report and Written Opinion of PCT/US2012/050877 dated Dec. 6, 2012.
Photographs of Johnson's Super Sudzer e-z grip soap purchased from Kroger stores around Aug. 2010 and believed to have been on the market in the US at least a year before the filing date of this application.
Photographs of Jonson's Buddies, easy-grip sudzing bar purchased from Target stores around Aug. 2010 and believed to have been on the market in the US at least a year before the filing date of this application.

* cited by examiner

PERSONAL CARE ARTICLES AND METHODS

TECHNICAL FIELD

The present disclosure generally relates to personal care articles and methods relating thereto.

BACKGROUND

Cleansing skin and/or hair is an activity that has been done for many years. Over time, skin and hair cleansing have involved the use of compositions such as bar and liquid soaps, body washes, shampoos, conditioners, and the like. For these compositions, consumers desirable good cleansing properties and lathering characteristics, mildness toward the skin, and the ability to provide benefit agents to the target surface.

To enhance a consumer's experience, such cleansing compositions can also be coupled with implements such as a washcloth, a sponge, or a puff. For example, many consumers dispense liquid soaps or body washes onto a puff and then cleanse by applying the puff to their skin and/or hair. Similarly, many consumers rub bar soaps with a washcloth and then cleanse by applying the washcloth to their skin and/or hair.

Although a consumer's experience with a cleansing composition can be enhanced by coupling the cleansing composition with an implement, to date, such an experience has not been completely ideal. For example, coupling such cleansing compositions with an implement tends to lead to clutter in the shower or bath as a consumer needs to carry or store cumbersome bottles, bars, jars, and/or tubes of cleansing products and the implements themselves. Additionally, coupling requires the user to perform additional steps of applying the body wash or soap on the implement and then rubbing or wiping the implement on their skin rather than just applying the body wash and/or soap directly. As such, more water tends to be consumed increasing the waste and carbon footprint of the consumer. And further, certain personal cleansing products, such as bar soaps, can have difficulty providing the consumer desired deposition of benefit agents, even when coupled with an implement.

Some attempts have been made to combine an implement with a personal cleansing composition in a personal cleansing article. However, these executions were not ideal. For example, one such article included a rigid bar soap coupled with an implement. The rigidity of this type of execution does not conform to the surface to which it is applied and making it difficult to thoroughly clean the target surface. Some other attempts at a more conformable product did not provide a desired reusability and tended to create additional waste. In particular, such cleansing articles tend lack durability and/or include cleansing compositions that completely dissolve after very few uses.

Accordingly, it would be desirable to provide a compliant personal care article that can have desirable cleansing properties, including suitable lathering and rinsing characteristics, can conform to the skin and/or hair, can be reusable and/or easy to use.

SUMMARY

In one embodiment, there is a personal care article, comprising: a compliant personal care composition; and a water penetrable first substrate adjacent to the composition; wherein the composition is greater than 3500 wt. %, by weight of the total substrate.

In another embodiment, there is a personal cleansing article, comprising: a compliant personal cleansing composition having a first side and a second side; a first substrate adjacent to one side of the personal cleansing composition; a second substrate adjacent to the other side of the personal cleansing composition; a first water insoluble substrate adjacent to the first substrate, and a second water insoluble substrate adjacent to the second substrate; wherein the composition has a compliance of about 0.03 to about 1.50 kg/mm.

In an additional embodiment, there is a compliant personal care article, comprising: about 4000 wt. % or more, by weight of total substrate, of a personal care composition; a first substrate surrounding the personal care composition and having a water flux rate of about 0.1 $cm^3/cm^2/s$ to about 60 $cm^3/cm^2/s$; and a second substrate surrounding the first substrate and having a water flux rate of about 0.1 $cm^3/cm^2/s$ to about 60 $cm^3/cm^2/s$; wherein the personal care article has a consumption rate of about 0.05 g/use to about 20 g/use.

These and other embodiments are more fully described in the description below.

DETAILED DESCRIPTION

I. Definitions

Figure 1:
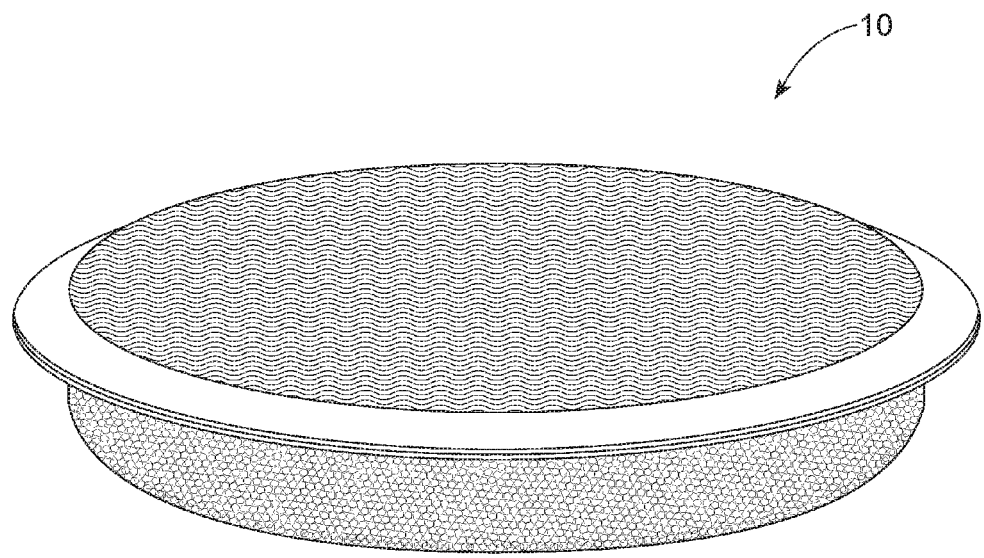
FIG. 1 depicts a perspective view of a personal care article according to one embodiment.

As used herein, the following terms shall have the meaning specified thereafter:

"Cleansing composition" refers to compositions intended for topical application to a surface such as skin and/or hair to remove, for example, dirt, oil, and the like. The cleansing compositions disclosed herein can be rinse-off formulations, in which the product is applied topically to the skin or hair via, for example, an implement or substrate and then subsequently rinsed within seconds to minutes from the skin and/or hair with water.

Compliant as used herein refers to an article and/or composition that at least partially conforms to a surface to which it is applied by some degree of deformation.

"g/use" refers to grams per use. This is the unit used for rate of consumption and the method for measuring and/or calculating it is described below.

"Macroapertured" refers to a substrate containing well-defined apertures having an average diameter of about 300 microns or greater.

"Microapertured" generally refers to a substrate containing well-defined microscopic apertures (i.e., those not readily visible to a naked eye having 20/20 vision).

"Natural" refers to materials that can be derived from plants, animals, insects, or materials that can be byproducts of plants, animals, or insects.

"Nonwoven" refers to a substrate comprising fibers not woven into a fabric but rather formed into a sheet. The fibers can either be random (i.e., randomly aligned) or the fibers can be non-random (for example, the nonwoven can be carded i.e. combed to be oriented in primarily one direction).

"Personal care" refers to a composition or article for topical application to skin and/or hair. Personal care compositions can be rinse-off formulations, in which the composition can be applied topically to the skin and/or hair and then subsequently rinsed within seconds to minutes of application. The composition could also be wiped off using a substrate. The personal care articles or compositions can also be used for cleansing of the skin, cleansing of the hair, shave preparation, post shave treatment, or a combination thereof.

"Reusable" refers to an article that can be used for a number of usage events, such as showers and/or baths, wherein the number of usage events can be about 5 or greater, about 7 or greater, about 10 or greater, about 15 or greater, about 20 or greater, about 25 or greater, or about 30 or greater.

"Substantially free of" refers to about 5% or less, about 3% or less, about 1% or less, or about 0.1% or less of a stated ingredient. "Free of" refers to no detectable amount of the stated ingredient or thing.

"Substrate" refers to a material which can limit the amount of water to which a personal care composition is exposed during a usage event versus exposure of a personal care composition itself absent a substrate. The substrate may be, for example, a film, formed film, batting, woven, nonwoven, or a combination thereof.

"Synthetic" refers to materials that can be obtained primarily from various man-made materials or from natural materials which have been altered.

"Usage event" refers to one 5 minute cycle of the Consumption Test below.

"Water insoluble substrate" refers to a substrate which does not dissolve in water during the life of the article.

II. Personal Care Article

Personal care compositions come in many forms. One of the more common forms is bar soap. Bar soap is generally non-compliant and rigid. The rigidity of most bar soaps make them difficult to grip making it more difficult to use during cleansing. Rigid bar soaps also have the disadvantage in that only the surface which directly contacts the skin can be used for cleansing and this surface area is limited by the bar's non-compliant nature. Conventional rigid bar soap has a compliance value of about 2.5 kg/mm or above.

Bar soaps are often used with an implement, like a wash cloth. At some point, a wrapped bar article was formed by combining the implement and the bar soap. Many of these previous attempts at a wrapped bar article maintained the non-compliant bar and thus still suffered from its short comings. Additionally, adding a wrap to conventional bar soap also had the unintended effect of reducing the consumption rate of the bar making cleansing difficult due to reduced access to the soap. The reduction in consumption also made the product last too long which meant the substrate could wear out before the bar was used up.

The insoluble components in bar compositions contribute to bar rigidity. Utilizing compliant compositions and/or articles forgoes the need for the rigidity and often results in the elimination of the insoluble components giving a faster dissolving composition. How quickly a composition dissolves is measured by its dissolution half life. For example, see the chart below.

|  | Dissolution half life |
| --- | --- |
| Commercial Ivory ® Bar soap (comparative) | 21.1 min. |
| Commercial Johnson's Bar soap (removed from interior of J&J Kids ® product) (comparative) | 17.8 min. |
| Inventive Example 15 | 3.3 min |
| Inventive Example 16 | 1.8 min |
| Inventive Example 3 | 3.5 min |
| Inventive Example 13 | 2.0 min |
| Inventive Example 17 | 10.1 min |
| Inventive Example 18 | 4.9 min |

While it is desirable to have a composition that provides sufficient cleaning properties during a cleansing event (i.e. dissolves well enough to release surfactant), there should be a balance between that and the longevity of the product. Otherwise, the product is entirely consumed in just one or a few events and the product is too expensive and wasteful to the environment.

How quickly a composition or article is used up by a consumer can be measured by its consumption rate, the method of which is described below. Substrates can be used to control the rate of consumption. So, when compositions dissolve quickly, substrates can be used to increase the consumption rate to a desirable level, like that of a typical bar soap. In the chart below, the effect of the addition of substrate(s) to some of the inventive compositions noted above is demonstrated.

| Consumption Rates | | | | | | |
| --- | --- | --- | --- | --- | --- | --- |
| Substrate | | | | | | |
| Interior (non-contact) | | Exterior (contact) | | | Total size of composition | Consumption rate of composition |
| First Substrate | Second Substrate | Third Substrate | Forth Substrate | Composition | or article (g) | or article (g/use) |
| none | none | none | none | Commercial Johnson's ® Bar soap | 72.8 | 4.6 |

-continued

Consumption Rates

| Substrate | | | | | | |
|---|---|---|---|---|---|---|
| Interior (non-contact) | | Exterior (contact) | | | Total size of composition | Consumption rate of composition |
| First Substrate | Second Substrate | Third Substrate | Forth Substrate | Composition | or article (g) | or article (g/use) |
| none | none | none | none | Commercial Dove ® Bar soap | 91.5 | 2.6 |
| none | none | none | none | Commercial Olay ® Bar soap | 100.6 | 3.9 |
| none | none | none | none | Commercial Safeguard ® Bar soap | 92.5 | 4 |
| F7 | F7 | F2 | Substrate B | Inventive Composition 3 | 13.3 | 2.9 |
| F7 | F7 | F2 | Substrate B | Inventive Composition 3 | 26.4 | 3.3 |
| F7 | F7 | F2 | Substrate B | Inventive Composition 3 | 51 | 2.8 |
| F7 | F7 | F2 | Substrate B | Inventive Composition 3 | 86.3 | 3 |
| F7 | F7 | F2 | Substrate B | Inventive Composition 3 | 143.8 | 3.7 |
| F7 | F7 | F2 | Substrate B | Inventive Composition 13 | 90 | 6.6 |
| F7 | F7 | F2 | Substrate B | Inventive Composition 16 | 102.3 | 6.4 |
| F7 modified by 50% Occluding (Sealed off) | F7 modified by 50% Occluding (Sealed off) | F2 | Substrate B | Inventive Composition 16 | 51.5 | 3.7 |

In the above inventive examples, the substrate is acting as a water flux limiting substrate to effectively increase their consumption rate. The water flux of the substrate may be manipulated by the chemical or physical make-up of the substrate. For example, the substrate may contain pores to allow more water passage. If less water passage is desired, the pore number may be reduced during manufacturing of the substrate or some of the pores may be sealed off. This is exemplified in the table below.

| Interior Substrate(s) (non-contact) | | | Water flux of | |
|---|---|---|---|---|
| First Substrate | Second Substrate | Composition | layer (cm³/cm²/s) | Consumption (g/use) |
| F2 | F2 | Inventive Example 16 | 33.8 | 10 |
| F7 | F7 | | 11.5 | 6.44 |
| F7 50% Occluded (Sealed off) | F7 50% Occluded (Sealed off) | | 5.8 | 3.7 |
| F7 90% Occluded (Sealed off) | F7 90% Occluded (Sealed off) | | 1.1 | 2.6 |

Additionally, it is desirable to minimize the environmental impact of consumer products. Body wash can exceed 80% water, increasing transportation impact and requiring a significant amount of plastic packaging material. Most consumers use an implement of some kind to facilitate cleansing when using a body wash. For example, a pouf comprising a bunched polyolefin scrim weighing about 30 grams is commonly used with body wash. The median lifetime of a pouf (in the U.S.) is about 3 months; thus, the environmental impact of the pouf can be about 0.33 grams polyolefin/day of waste material generated. The total environmental impact of body wash and pouf can be considerably greater if packaging materials are included.

Compliant articles can provide an improved environmental footprint compared to a pouf. Some compliant articles can provide half or even less plastic waste material per shower than a pouf. The tables below shows compliant articles having about 850 wt % cleansing composition by total weight of substrate provide comparable contribution to the waste stream as a pouf. However, when the composition amount is increased to greater than 1,000 wt %, consumption rate remains comparable to a bar of soap with the same amount of wrapping material, providing significant non biodegradable waste improvements to a pouf. Moreover, when the amount of composition by weight of total substrate is increased to about 3500 wt % or more, there is a significant improvement in both waste and in the number of uses.

| Substrate | | | | | | | | | | |
|---|---|---|---|---|---|---|---|---|---|---|
| Interior (non-contact) | | Exterior (contact) | | | Total size | Consumption | Chem. Comp. % of total | | waste | |
| 1st Substrate | 2nd Substrate | 3rd Substrate | 4th Substrate | Composition | of article (g) | (g/use) | substrate weight | # uses | wrap wt. (g) | Waste/day (g) |
| F7 Water Flux of Substrate (cm³/cm²/s) 11.5 | F7 Water Flux of Substrate (cm³/cm²/s) 11.5 | F2 Water Flux of Substrate (cm³/cm²/s) 33.8 | Substrate B Water Flux of Substrate (cm³/cm²/s) 2.6 | Inventive Comp. 3 | 13.3 26.4 51 86.3 143.8 | 2.92 3.33 2.8 3.04 3.72 | 848% 1783% 3543% 6061% 10174% | 4 7 18 28 38 | 1.4 1.4 1.4 1.4 1.4 | 0.34 0.19 0.079 0.05 0.037 |

A personal care article comprises a substrate and a personal care composition. The personal care article may also comprise multiple substrates. The personal care article may be used, for example, on skin, hair, or both. The personal care article may also be used, for example, for cleansing of the skin, cleansing of the hair, shave preparation, post shave treatment, or a combination thereof. In one embodiment, the personal care article is a personal cleansing article. In one embodiment, the personal care article is reusable.

The personal care article can be compliant (i.e. it at least partially conforms to a surface to which it is applied by some degree of deformation.) For example, if the article is a personal care article for cleansing the skin, then the article will bend to some degree to more fully contact a curved body part like the arm. Thus, if the personal care article is originally flat with no curve, when applied to the arm for cleansing there would be some amount of bend to better conform to the arm. Likewise, if the article's shape has a small amount of a curve, when applied to the arm the article would bend to some degree to more fully contact the arm. Oppositely, if the original article is curved such that it would not need to bend to conform to a curved surface like the arm, then it would bend to straighten when applied to a less curved surface like the abdomen. In one embodiment, the article and/or composition is fully compliant meaning it is capable of completely conforming to the surface to which it is applied.

In some embodiments, the compliant article will comprise a particulate composition. A particulate composition can be made of smaller particles like sand, larger particles like pellets, or anything in-between, and combinations thereof. These compositions may be formless and thus rely on a substrate or substrates to house them for use. For these types of articles, it is the ability of the composition in combination with the substrate(s) to at least partially deform to the shape of the surface to which it is applied that makes them compliant.

In some embodiments, compliance of the article can be measured according to the test described in more detail below. In some embodiments, a personal care article can comprise a compliance value of about 1.50 kg/mm or less. In varying embodiments, the compliance value of the article is about 1.35 kg/mm or less; about 1.25 or less; about 1.2 or less; about 1.1 or less; or about 1.0 or less. In additional embodiments, the article has a compliance of about 0.01 kg/mm to about 1.50 kg/mm; about 0.03 kg/mm to about 1.50 kg/mm; about 0.05 kg/mm to about 1.25 kg/mm; about 0.05 kg/mm to about 1.15 kg/mm; about 0.10 to about 1.1; or any combination thereof.

The personal care composition can also be compliant similar to what is discussed above for the article. For example, if the composition is a personal cleansing composition for cleansing the skin, then the composition will bend to some degree to more fully contact a curved body part like the arm. Thus, if the personal cleansing composition is originally flat with no curve, when applied to the arm for cleansing there would be some amount of bend to better conform to the arm. Likewise, if the composition's shape has a small amount of a curve, when applied to the arm the composition would bend to some degree to more fully contact the arm. Oppositely, if the original composition is curved such that it would not need to bend to conform to a curved surface like the arm, then it would bend to straighten when applied to a less curved surface like the abdomen.

In some embodiments, compliance of the composition can be measured according to the test described in more detail below. In some embodiments, a personal care composition can comprise a compliance value of about 1.50 kg/mm or less. In varying embodiments, the compliance value of the composition is about 1.35 kg/mm or less; about 1.25 or less; about 1.2 or less; about 1.1 or less; or about 1.0 or less. In additional embodiments, the composition has a compliance of about 0.01 kg/mm to about 1.50 kg/mm; about 0.03 kg/mm to about 1.50 kg/mm; about 0.05 kg/mm to about 1.25 kg/mm; about 0.05 kg/mm to about 1.15 kg/mm; about 0.10 to about 1.1; or any combination thereof.

In some embodiments, the composition and/or article may become compliant after exposure to water. Thus, you may have a non-compliant composition or article that, after exposure to a liquid, like water, during a usage event, becomes compliant. If an article and/or composition become compliant by the end of a second usage event, then they are considered compliant according to this application.

The personal care article will have a rate of consumption. This is a measure of how much of the composition is used during a usage event. A method for measuring consumption rate of the article is described in more detail below. In one embodiment, the article will have a consumption rate of about 20 g/use or less. In another embodiment, the article will have a consumption rate of about 15 g/use or less. In alternate embodiments, the article will have a consumption rate of about 1.5 g/use to about 15 g/use; from about 2.5 g/use to about 10 g/use; from about 3.5 g/use to about 6.5 g/use, or any combination thereof.

Figure 4:
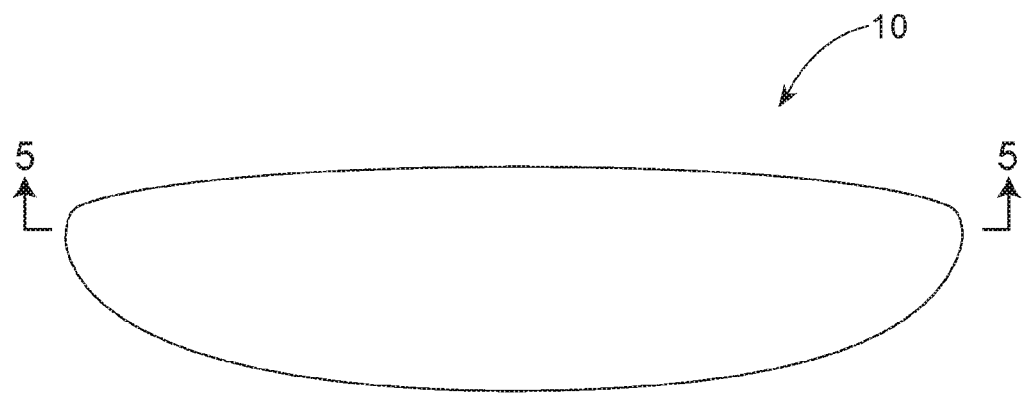
FIG. 4 depicts a side view of a personal care article according to another embodiment.
Figure 5A:
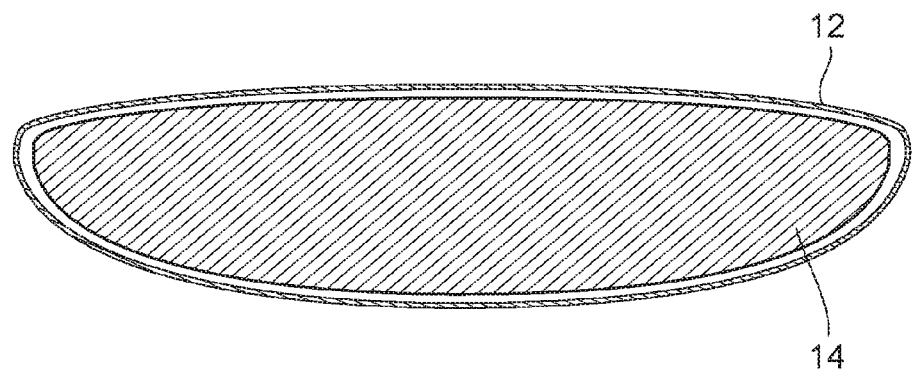
FIG. 5A depicts a cross sectional view of the personal care article of FIG. 4, along line 5-5.
Figure 5B:
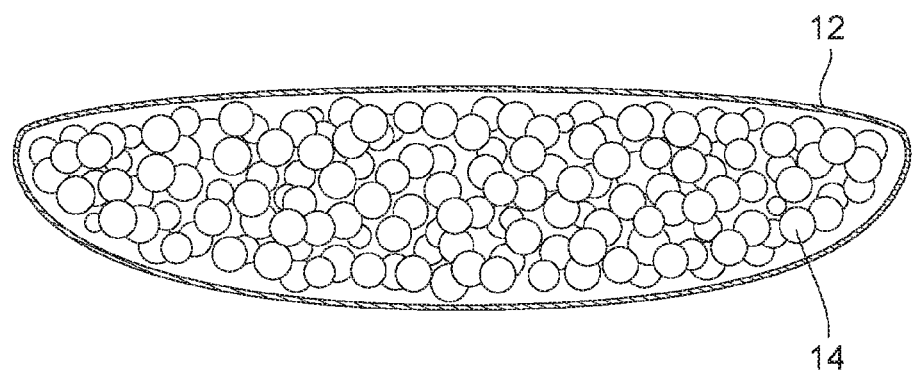
FIG. 5B depicts a cross sectional view of the personal care article of FIG. 4, along line 5-5, where the composition is in the form of pellets.

A perspective view of a person care article 10 according to one embodiment is shown in FIG. 1. As shown in FIGS. 4, 5A, and 5B, the personal care article 10 can comprise a water penetrable first substrate 12 and a personal care composition 14, wherein the water penetrable first substrate 12 is adjacent to the personal care composition 14. The water penetrable first substrate 12 at least partially surrounds the composition 14. In one embodiment, as shown in FIG. 4, a single piece of water penetrable substrate 12 has been wrapped around the personal care composition 14 and sealed (not shown). In FIG. 5B, the composition 14 is in the form of pellets.

Figure 2:
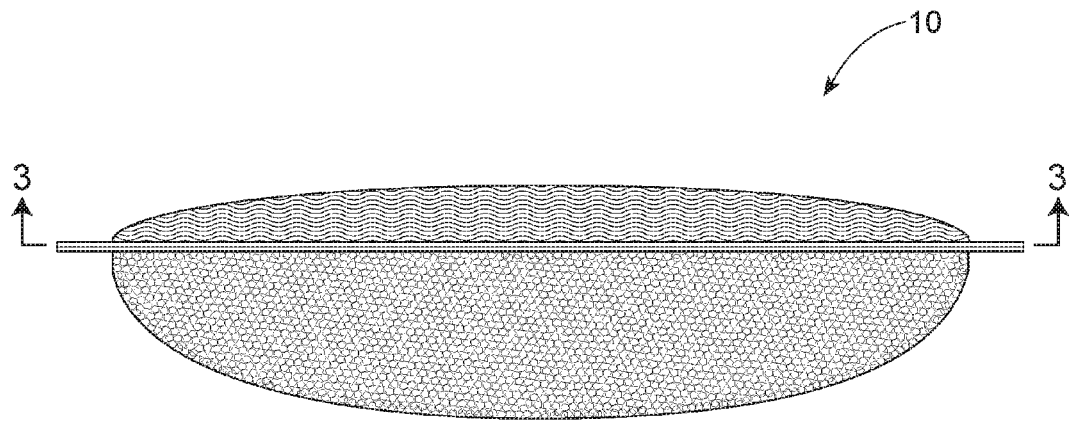
FIG. 2 depicts a side view of a personal care article according to one embodiment.
Figure 3A:
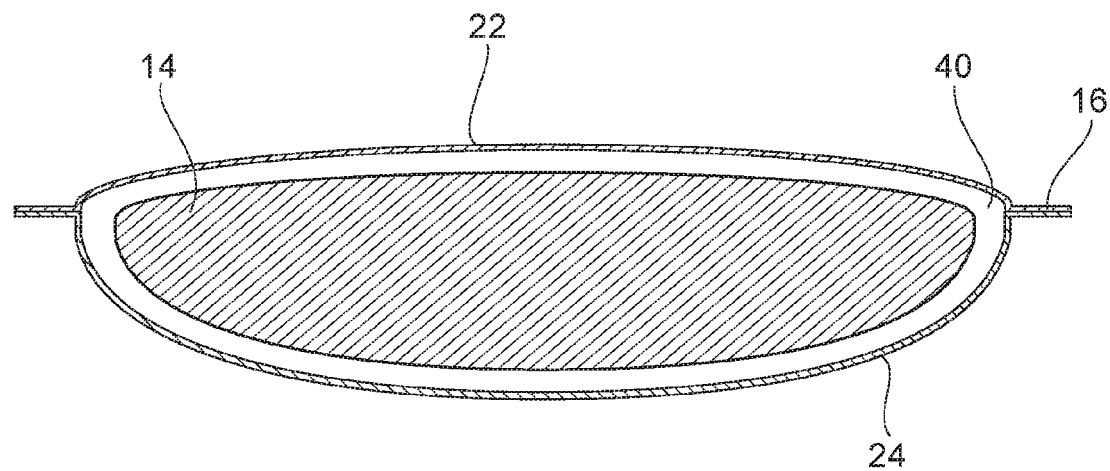
FIG. 3A depicts a cross sectional view of the personal care article of FIG. 2, along line 3-3.

In another embodiment, as illustrated in FIGS. 2 and 3A, a personal care article 10 comprises a personal care composition 14, a first substrate 22 adjacent to the personal care composition 14, and a second substrate 24 adjacent to the personal care composition 14. In one embodiment depicted in FIG. 3A, the seal 16 joining the first and second substrates (22, 24) is only visible on the ends, but actually goes all the way around the personal care composition 14. The first and second substrates (22, 24) may, however, may be sealed in other configurations, or, may only be partially sealed so as to form, for example, a pouch. The first and second substrates (22, 24) may be the same or different.

Figure 3B:
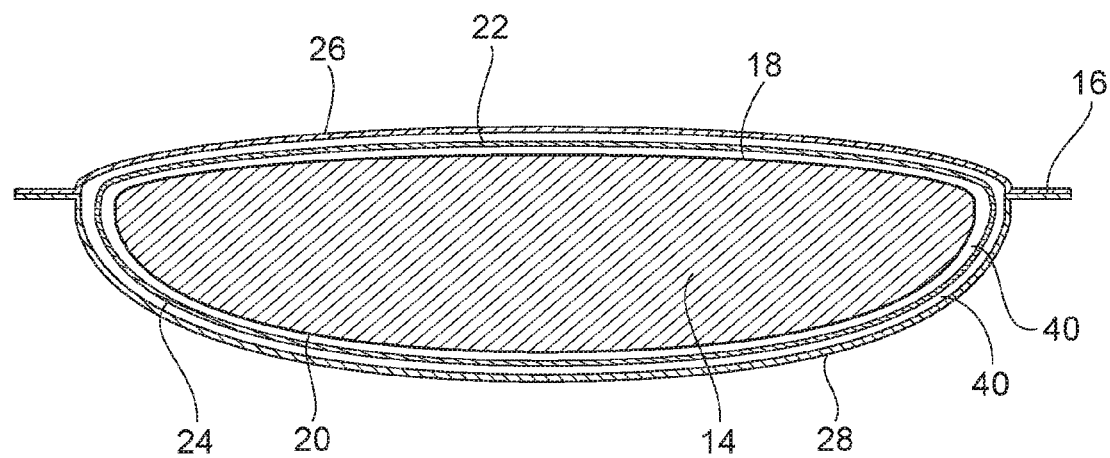
FIG. 3B depicts a cross sectional view of the personal care article of FIG. 2, along line 3-3, where additional substrates have been added.

In another embodiment, as illustrated in FIGS. 2 and 3B, a personal care article 10 comprises a personal care composition 14 having a first side 18 and a second side 20. A first substrate 22 is adjacent to the first side 18, while a second substrate 24 is adjacent to the second side 20. In one embodiment depicted in FIG. 4, the seal 16 joining the first and second substrates (22, 24) is only visible on the ends 30, but actually goes all the way around the personal care composition 14. In addition, a first water insoluble substrate 26 is adjacent to the first substrate 22 and a second water insoluble substrate 28 is adjacent to the second substrate 24. The first and second water insoluble substrates (26, 28) may be the same or different. Like the seal of the first and second substrate (22, 24), while only visible on the ends, the seal 16 of the first and second water insoluble substrates (26, 28) goes all the way around the personal care composition 14. The seal 16 of the first and second water insoluble substrate (26, 28) may, however, be sealed in other configurations, or, may only be partially sealed so as to form, for example, a pouch.

The personal care article may also comprise a chamber 40, as seen, for example, in FIGS. 3A and 3B. A chamber is open area between a substrate and a personal care composition or between a substrate and another substrate, where the substrate is not touching the personal care composition or the other substrate. The substrate(s) may be flexible such that they touch the composition (or another substrate) in some areas and not others. The areas where the substrate is touching or not touching the composition or other substrate may shift as the substrate(s) and composition shift during handling and/or use.

The personal care article can include from about 0.5% to about 25,000%, by weight of total substrate(s), of a personal care composition. In one embodiment, the article comprises greater than 3,500%, by weight of the total substrate(s), of a composition. In another embodiment, the article comprises greater than 4,000%, by weight of the total substrate(s), of a composition. In varying embodiments, the article comprises greater than 4,250%, by weight of the total substrate(s), of a composition; greater than 4,500%, by weight of the total substrate(s), of a composition; greater than 4,750%, by weight of the total substrate(s), of a composition; greater than 5,000%, by weight of the total substrate(s), of a composition; or any combination thereof.

The personal care article may be in any suitable shape, for example, oval, square, rectangular, circular, triangular, hour glass, hexagonal, c-shaped, etc.

A. Substrate

The personal care article comprises at least one substrate. The substrate can enhance cleansing and therapeutic treatment of a surface such as skin and/or hair. For example, by physically coming into contact with the skin and/or hair, the substrate can aid in the cleansing and removal of dirt, makeup, dead skin, and other debris such that the substrate can act as an efficient lathering and/or exfoliating implement but can also be non-abrasive to the skin. A substrate can be a composite (i.e. there are multiple plies to the substrate which may be of the same or different materials). In one embodiment, the substrate is water insoluble. In other embodiments, the substrate is water penetrable.

In one embodiment, a substrate at least partially surrounds a personal care composition. In another embodiment, a substrate surrounds a personal care composition. In additional embodiments, a substrate is in the form of a pouch, pocket, wrap, or a combination thereof.

A substrate may be a contact substrate, which is a substrate for contacting a target surface, like the skin for example. A substrate may also be a noncontact substrate. Noncontact substrates may, for example, be used to help give a personal care article the desired consumption rate, softness, lather properties, etc.

The substrate may be water penetrable. Where the substrate is water penetrable, the substrate will have a water flux rate. The water flux rate can be used to limit wetting of the cleansing composition included in the personal care article thereby controlling lather, dissolution, and/or consumption of the composition included in the personal care article. Without being limited by theory, the first substrate can manage or limit the water flux rate to provide controlled wetting and to extend a useful life of the personal care composition while still enabling enough wetting to provide, for example, suitable lather. In certain embodiments, the water flux rate can be from about 0.1 $cm^3/cm^2/s$ to about 200 $cm^3/cm^2/s$, from about 0.4 $cm^3/cm^2/s$ to about 120 $cm^3/cm^2/s$, from about 20 $cm^3/cm^2/s$ to about 100 $cm^3/cm^2/s$, or any combination thereof, as measured by the water flux rate test disclosed below. The ability to control the water flux rate allows for adjustment such that the composition, like a cleansing composition, can be reused and, thus, last through a number of shower, bathing or cleansing experiences while still exhibiting lathering characteristics expected by consumers.

In some embodiments, there will be a water flux differential between substrates. In varying embodiments, the flux differential between substrates is at least about 2.5 $cm^3/cm^2/s$; about 3.0 $cm^3/cm^2/s$ or more; or about 4.0 $cm^3/cm^2/s$ or more.

The substrate will, in some embodiments, need a sufficient tensile strength in order to effectively fulfill its desired role. For example, a contact substrate may need to have a higher tensile strength than a noncontact substrate due to its contact with the target surface. In one embodiment, a substrate can provide an ultimate tensile strength of about 10 g/mm width or greater, about 30 g/mm (width) or greater, about 60 g/mm (width) or greater, or about 200 g/mm (width) or greater and a stiffness of about 1 g/mm (width) or greater, about 2 g/mm (width) or greater, about 7 g/mm (width) or greater, about 20 g/mm (width) or greater, or about 80 g/mm (width) or greater.

The substrate can further provide a variety of textures. Texturized substrates can be used for both contact and noncontact substrates. In one embodiment, the article can have a different texture on each side thereof. For example, the article can include a gripping side and a substrate application side. In one embodiment, the gripping side can include a texture that is the same as the substrate application side. In another embodiment, the gripping side can include a texture that is different than the substrate application side.

In certain embodiments, the substrate can be a nonwoven (i.e. a natural or synthetic nonwoven including fibrous and nonfibrous nonwovens), a woven, a film (e.g. a formed film), a sponge (e.g. a natural and/or synthetic sponge), a polymeric netted mesh (i.e. a "scrim"), a batting, spunbond, spunlace, hydroentangled, carded, needlepunch, or any other suitable material.

Suitable formed films for use as a substrate in the personal care article can include plastic formed films, such as polyolefins, including, for example, low density polyethylene (LDPE) films, hydroapertured polyethylene films with one or more openings such as apertures of from about 0.1 mm to about 3 mm, and combinations thereof. Many of such films are available from Tredegar, Inc.

When selecting formed films, some parameters to consider include: thickness, pattern, polymer stiffness, and permeability. Thickness can be measured by physical measurement of the thickness (like by using a caliper) or basis weight. In one embodiment, the thickness of the film substrate is from about 1.5 mm to about 5 mm. In another embodiment, the film substrate has a basis weight from about 10 g/m$^2$ to about 100 g/m$^2$. The pattern of the film substrate may also be important. For cleansing embodiments, a square or hex pattern gives better properties of appearance and cleansing ability.

Polymer stiffness of formed films affects texture and bending. When looking at polymer stiffness, $T_g$, glass transition temperature, is a good indicator. In one embodiment, a polymer used to form a film substrate has a $T_g$ of about −20° C. to about −125° C. Also, depending on other factors, like the desired consumption rate of the article, the permeability of a formed film can be important. Permeability is often measured as the rate of flux of a fluid through a substrate under a standard set of conditions. A test for determining water flux is below. In one embodiment, a film substrate has a pore open area of about 2% to about 20%.

The substrate can also be a nonwoven. A nonwoven typically has land regions (i.e. regions that do not allow water and/or the cleansing composition to pass through) and openings. In one embodiment, the nonwoven can provide sufficient air space between, for example, openings and land regions of the substrate and can help control permeability of the substrate. The nonwoven substrate can be fibrous or nonfibrous.

Suitable fibrous nonwovens for use as a substrate in a personal care article can include a spunlaid hydroentangled 100% polypropylene (PP) available from Avgol Nonwovens, N.C., USA; a carded, calendar bonded all bi-component polypropylene/polyethylene (PP/PE) fiber available from Fiberweb Inc., TN, USA; a spunbond, overbonded 100% PP, and a carded, through air bonded 30/30/40 PP/Bi-component PP-PE/Rayon.

An additional nonwoven suitable for use as a substrate herein includes batting fibers which can include fusible battings. Fusible battings may be fused, for example, by thermoplastic adhesives or via bicomponent fibers. For example, a nonwoven substrate can include a low loft all polyester batting available from Fairfield Processing, Danbury, Conn., USA; a low loft all polyester, ½ thickness (peeled) batting available from Fairfield Processing, Danbury, Conn., USA; a PROEF 12-334 polyester-bicomponent fiber blend batting available from Libeltex, Belgium; a PROEF 12-370 dual layer PET/copet bico and PP fibers available from Libeltex, Belgium; a bulk layer with standard PET/coPET bicotrilobal fibers available from Libeltex, Belgium; a dry web T30 SC batting, hollow PET+bico PET/PE fiber blend, air bonded available from Libeltex, Belgium; a PROEF 12-372 batting, coarse polyester and PE/PET bico fibers available from Libeltex, Belgium; and a dry web T23W batting, coarse polyester and bico fiber mix available from Libeltex, Belgium.

Polymeric netted meshes or scrims can also be useful as a substrate for a personal care article. Some examples can include those described in U.S. Pat. No. 4,636,419. In one embodiment, the substrate comprises a polypropylene scrim or a polyethylene scrim. In a further embodiment, the substrate comprises a low density polyethylene scrim.

A substrate may comprise a polymeric mesh sponge. Some suitable polymeric mesh sponges are described in European Patent Application No. EP 702550A1 published Mar. 27, 1996. Polymeric mesh sponges can comprise a plurality of plies of an extruded tubular netting mesh prepared from a strong flexible polymer, such as addition polymers of olefin monomers and polyamides of polycarboxylic acids.

In certain embodiments, a substrate can also be a composite material that includes, for example, one or more plies of the same or different materials such as nonwovens, wovens, films, sponges, scrims, battings, and the like superimposed physically, joined together continuously (e.g., laminated, etc.) in a discontinuous pattern, or by bonding at the external edges (or periphery) of the substrate and/or at discrete loci. The substrate can be a composite material comprising at least one formed film and at least one non-woven where the substrate can be vacuum-formed. Such a suitable formed film composite material can include, for example, a vacuum-laminated composite formed film material that can be made or formed by combining a carded polypropylene nonwoven having a basis weight of 30 gm$^2$ with a formed film.

Additionally, as described above, a substrate can include one or more openings such that water, the composition, and/or lather, for example, can pass through the substrate. In one embodiment, where the permeable substrate is adjacent to the composition, the water passes through the water permeable substrate to interact with the personal care composition. As the composition dissolves, it will then also pass through the substrate to be delivered to the target surface, like the skin.

In one embodiment, the permeability of the openings can be selected based on the dissolution half life of the personal care composition and the desired reusability of the article. For example, when the dissolution half life of the personal care composition is high, a higher level of permeability can be selected to counteract the high dissolution half life and provide a desirable consumption rate for the article. Alternatively, when the dissolution half life of the personal care composition is low, the permeability of the one or more openings or can be lower and still provide a desirable consumption rate for the article. In varying embodiments, a substrate can include a permeability of about 1 opening/cm$^2$ or greater, about 10 openings/cm$^2$ or greater, about 100 openings/cm$^2$ or greater, about 500 openings/cm$^2$ or greater, about 1,000 openings/cm$^2$ or greater, about 1,500 openings/cm$^2$ or greater, or any combination thereof.

The openings can be apertured, nonapertured, or a combination thereof. For example, the one or more openings can include well-defined apertures such as microapertures or macroapertures, holes, perforations, cavities, raised or depressed fibrous and/or nonfibrous regions, gaps between regions, and the like that can enable, for example, water and/or the cleansing composition to pass through the substrate.

In one embodiment, a personal care article comprises more than one substrate. In one embodiment, a personal care article comprises more than one contact substrate. A combination of contact substrates may be used, for example, to give different properties to different sides of an article. Using FIG. 3B as an example, the first water insoluble substrate 26 may be a contact substrate which helps gripping and the second water insoluble substrate 28 may be a contact substrate on another portion of the article selected for its application properties. As another example, in one embodiment, the article has an exfoliating contact substrate on one side of the article and a soothing contact substrate on the other side.

A personal care article may also comprise more than one substrate where one substrate comprises a contact substrate and another substrate a noncontact substrate. Using FIG. 3B as an example, the first and second water insoluble substrates 26, 28 would both be contact substrates, while the first and second substrates 22, 24 would be noncontact substrates. In one embodiment, a noncontact substrate is at least partially surrounded by at least one contact substrate. In another embodiment, two noncontact substrates are surrounded by two contact substrates. Additional contact and non-contact substrates may also surround other substrates and/or a composition.

A combination of substrates can be used to not only give different user experience properties, like exfoliating versus soothing, but it may also be used to give other desirable properties of an article, like appropriate consumption rate and lather. When combining substrates to form an article, one should consider the properties of the composition, in addition to the individual properties of the substrates, to come up with the article with the desired properties. For example, in one embodiment, a personal care composition is surrounded by two noncontact substrates which are surrounded by two contact substrates. In a further embodiment, the two noncontact substrates are the same. In a further embodiment, the two contact substrates are the same.

Some examples of suitable substrates are included below.

B. Personal Care Composition

As noted above, a personal care article comprises a substrate and a personal care composition. The personal care composition may be a rinse-off composition, for example a cleanser, or a leave-on composition, for example a moisturizer.

In one embodiment, the personal care composition is compliant as discussed above. The personal care composition may have a compliance value 0.01-1.50 kg/mm.

In some embodiments, the personal care composition will have a dissolution half life. In varying embodiments, the personal care composition has a dissolution half life of about 1.0 min. to about 15 min.; about 1.1 min. to about 13 min.; from about 1.2 min. to about 12 min.; about 1.3 min. to about 11 min.; about 1.4 min. to about 8.0 min.; about 1.5 min. to about 5 min.; or any combination thereof.

The personal care composition may be adjacent to one or more substrates. For example, the personal care article can include a composition disposed between the one or more substrates. As shown in FIG. 3A, the composition 14 can be disposed within and adjacent to the water penetrable first substrate 12 such that the first substrate 12 can surround the cleansing composition 14. As described above, the substrate can activate and/or engage the composition.

The composition may be in the any suitable form. For example, the composition may be in the form of a bar, paste, gel, pellets, beads, or a combination thereof. Additionally, the composition may be of any shape desirable to a user.

The personal care composition may be, for example, a cleansing composition, a moisturizing composition, a pre-shave composition, a post-shave composition, a shampoo, a conditioner, or a combination thereof. In one embodiment, the personal care composition comprises a personal cleansing composition.

In varying embodiments, the personal cleansing composition comprises a synthetic surfactant, a soap, or a combination thereof.

1. Synthetic Cleansing Compositions

In one embodiment, the cleansing composition can comprise a synthetic surfactant. In a further embodiment, the surfactant comprises a mixture of surfactants and the composition further comprises a rheology modifier.

The cleansing composition can also include about 1 gram or more, about 5 grams or more, or about 10 grams or more, by weight of the total substrate, of a surfactant if, for example, the cleansing composition can be added to the water insoluble substrate or wrap without requiring a drying process. In another embodiment, the cleansing composition can include from about 1% to about 99.5% or from about 10% to about 70%, by weight of the cleansing composition, of a surfactant or a mixture of surfactants.

Suitable synthetic surfactants for a personal cleansing composition include, for example, linear alkyl sulfates, branched alkyl sulfates, linear alkyl ether sulfates, branched alkyl ether sulfates, linear alkyl sulfonates, branched alkyl sulfonates, linear alkyl ether sulfonates, branched alkyl ether sulfonates, or a combination thereof.

Some additional suitable synthetic surfactants include, for example, anionic, nonionic, cationic, zwitterionic, amphoteric surfactants, or combinations thereof. For example, according to one embodiment, the synthetic surfactant can comprise an anionic surfactant. The anionic surfactant can be branched or linear. Examples of suitable linear anionic surfactants include ammonium lauryl sulfate, ammonium laureth sulfate, sodium lauryl sulfate, sodium laureth sulfate, potassium laureth sulfate, sodium lauryl sarcosinate, sodium lauroyl sarcosinate, sodium cocoyl isethionate, lauryl sarcosine, cocoyl sarcosine, ammonium cocoyl sulfate, potassium lauryl sulfate, or combinations thereof.

In one embodiment, the synthetic surfactant can comprise sodium laureth(n) sulfate, hereinafter SLEnS, where n defines the average moles of ethoxylation. In another embodiment, the synthetic surfactant can comprise sodium trideceth(n) sulfate, hereinafter STnS, wherein n defines the average moles of ethoxylation. According to example embodiments, n for the SLEnS and/or the STnS can range from about 0 to about 8, from about 1 to about 3, about 2, or about 1. It will be understood that a material such as SLEnS or STnS can comprise a significant amount of molecules having no ethoxylate, 1 mole ethoxylate, 2 mole ethoxylate, 3 mole ethoxylate, and so on in a distribution which can be broad, narrow, or truncated. For example, SLE1S can comprise a significant amount of molecules which have no ethoxylate, 1 mole ethoxylate, 2 mole ethoxylate, 3 mole ethoxylate, and so on in a distribution which can be broad, narrow, or truncated and still comprise SLE1S where an average distribution can be about 1. Similarly, ST2S can comprise a significant amount of molecules which have no ethoxylate, 1 mole ethoxylate, 2 mole ethoxylate, 3 mole ethoxylate, and so on in a distribution which can be broad, narrow, or truncated and still comprise ST2S, where an average distribution can be about 2.

The synthetic surfactant can also comprise one or more branched anionic surfactants and monomethyl branched anionic surfactants such as sodium trideceth sulfate, sodium tridecyl sulfate, sodium C12-13 alkyl sulfate, C12-13 pareth sulfate, sodium C12-13 pareth-n sulfate, or combinations thereof.

As described above, in other embodiments, the synthetic surfactant can comprise a nonionic surfactant. Nonionic surfactants for use in the cleansing composition can include those selected from the group consisting of alkyl glucosides, alkyl polyglucosides, polyhydroxy fatty acid amides, alkoxylated fatty acid esters, sucrose esters, amine oxides, or mixtures thereof.

In another embodiment, the synthetic surfactant can comprise a cationic surfactant. Cationic surfactants for use in a synthetic cleansing composition include, but are not limited to, fatty amines, di-fatty quaternary amines, tri-fatty quaternary amines, imidazolinium quaternary amines, or combinations thereof.

The synthetic surfactant can also comprise an amphoteric surfactant. Suitable amphoteric surfactants can include those that are broadly described as derivatives of aliphatic secondary and tertiary amines, in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition can include sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378. In one embodiment, the surfactant included in the personal care composition can comprise an amphoteric surfactant that can be selected from the group consisting of sodium lauroamphoacetate, sodium cocoamphoactetate, disodium lauroamphoacetate disodium cocodiamphoacetate, and mixtures thereof.

The synthetic surfactant can also comprise a zwitterionic surfactant. Suitable zwitterionic surfactants can include those that are broadly described as derivatives of aliphatic quaternary ammonium, phosphonium, and sulfonium compounds, in which the aliphatic radicals can be straight or branched chain, and wherein one aliphatic substituent contains from about 8 to about 18 carbon atoms and one contains an anionic group, e.g., carboxy, sulfonate, sulfate, phosphate, or phosphonate. In one embodiment, the zwitterionic surfactant included in the composition can comprise one or more betaines such as cocoamidopropyl betaine.

In one embodiment, a synthetic cleansing composition further includes a soap.

2. Soap Compositions

In another embodiment, the cleansing composition can comprise soap.

In varying embodiments, the cleansing composition can include from about 40% to about 99.5%, from about 45% to about 75%, from about 50% to about 65%, or any combination thereof, by weight of the cleansing composition, of a soap.

The soap can include, for example, alkali metal or alkanol ammonium salts of alkane- or alkene monocarboxylic acids. Sodium, magnesium, potassium, calcium, mono-, di- and tri-ethanol ammonium cations, or combinations thereof, can be suitable. In one embodiment, the soap comprises a sodium soap. In another embodiment, the soap comprises a sodium soap and from about 1% to about 25% of at least one of ammonium, potassium, magnesium, and calcium soap. In certain embodiments, suitable soaps can include the well-known alkali metal salts of alkanoic or alkenoic acids having from about 12 to 22 carbon atoms, from about 12 to about 18 carbon atoms; or alkali metal carboxylates of alkyl or alkene hydrocarbons having from about 12 to about 22 carbon atoms.

The cleansing composition can also include soaps having a fatty acid distribution of coconut oil that can provide a lower end of a broad molecular weight range or a fatty acid distribution of peanut or rapeseed oil, or their hydrogenated derivatives, which can provide an upper end of the broad molecular weight range.

In one embodiment, a soap in the cleansing composition can include a fatty acid distribution of tallow and/or vegetable oil. The tallow can include fatty acid mixtures that typically have an approximate carbon chain length distribution of 2.5% C14, 29% C16, 23% C18, 2% palmitoleic, 41.5% oleic, and 3% linoleic. The tallow can also include other mixtures with similar distribution, such as the fatty acids derived from various animal tallows and/or lard. According to an example embodiment, the tallow can also be hardened (i.e., hydrogenated) to convert part or all of the unsaturated fatty acid moieties to saturated fatty acid moieties.

In one embodiment, the vegetable oil can be selected from the group consisting of palm oil, coconut oil, palm kernel oil, palm oil stearine, and hydrogenated rice bran oil, or mixtures thereof. In another embodiment, the vegetable oil is selected from the group consisting of palm oil stearine, palm kernel oil, coconut oil, and combinations thereof. According to one embodiment, the coconut oil can include a proportion of fatty acids having 12 carbon atoms or more of about 85%. Such a proportion can be greater when mixtures of coconut oil and fats such as tallow, palm oil, or non-tropical nut oils or fats are used where the principle chain lengths can be C16 and higher. According to one embodiment, the soap included in the cleansing composition can be a sodium soap having a mixture of about 67-68% tallow, about 16-17 coconut oil, and about 2% glycerin, and about 14% water.

In one embodiment, the soap included in the cleansing composition can be made by a classic kettle boiling process or modern continuous soap manufacturing processes wherein natural fats and oils such as tallow or coconut oil or their equivalents can be saponified with an alkali metal hydroxide using procedures well known to those skilled in the art. Alternatively, the soaps can be made by neutralizing fatty acids such as lauric (C12), myristic (C14), palmitic (C16), or stearic (C18) acids with an alkali metal hydroxide or carbonate.

For example, the cleansing composition can include a soap made by a continuous soap manufacturing process. The soap can be processed into soap noodles via a vacuum-flash drying process. In one embodiment, a soap noodle useful herein can include about 67.2% tallow soap, about 16.8% coconut soap, about 2% glycerin, and about 14% water. In another embodiment, a soap noodle can be a vegetable based soap noodle comprising about 66.87% sodium palmate, about 16.72% sodium cocoate, about 5.22% glycerin, about 0.40% sodium chloride, about 0.19% palm acid, about 0.10% coconut acid, about 0.03% pentasodium pentetate, about 0.03% tetrasodium etidronate, and about 10.45% water. These percentage amounts are by weight of the soap noodles. The soap noodles can then be utilized in a milling process to make finished soap useful in the cleansing composition.

In one embodiment, a soap containing cleansing composition may further comprise a synthetic surfactant, several examples of which are described above.

3. Other Ingredients for Cleansing Compositions

The cleansing compositions disclosed herein can also include one or more optional ingredients such as humectants, rheology modifiers, polymers, gums, block copolymers, inorganic salts such as zinc carbonate, antimicrobial agents, actives, brighteners, silica, moisturizers or benefit agents, emulsifiers, or combinations thereof, as described below.

The cleansing composition can further include a humectant. In one embodiment, the humectant comprises glycerin. In one embodiment, the humectant can maintain and/or provide a particular rheology for the cleansing composition such that the cleansing composition can be manipulated to conform to and/or mimic the surface of the substrate to which the personal cleansing article is being applied.

In one embodiment, the cleansing composition can include from about 10% to about 90% or from about 25% to about 75%, by weight of the cleansing composition, of a humectant. Suitable humectants can include glycerin; sorbitol; propylene glycol; butylene glycol; hexylene glycol; ethoxylated glucose; 1,2-hexane diol; hexanetriol; dipropylene glycol; Erythritol; starch; trehalose; diglycerin; xylitol; maltitol; maltose; glucose; fructose; sodium chondroitin sulfate; sodium hyraluronate; sodium adenosin phosphate; sodium lactate; pyrrolidone carbonate; glucosamine; cyclodextrin; salts such as chlorides, sulfates, carbonates; or combinations thereof. In one embodiment, a cleansing composition comprises about 20% or more, by weight of the composition, of glycerin. In varying embodiments, the composition comprises about 25% or more, about 30% or more, about 40% or more, about 45% or more, by weight of the composition, of glycerin.

The cleansing composition can further include a rheology modifier. Similar to the humectant, the rheology modifier can maintain and/or provide a particular rheology for the cleansing composition such that the cleansing composition can be manipulated to conform to and/or mimic the surface of the substrate to which the personal cleansing article is being applied.

Suitable rheology modifiers for use in the personal cleansing composition can include clays, starches, polymers (natural, synthetic, and/or copolymers), and the like. Suitable clays for use in the cleansing composition include, for example, both natural and modified clays such as montmorillonite and laponite. Additionally, suitable starches for use in the cleansing composition described here can include carbohydrates such raw starch (corn, sago, rice, potato, wheat, and the like) and pregelatinized starch and suitable polymers for use in the cleansing composition disclosed here can include structuring polymers such as hydrophobically modified polymers, which are described in more detail below.

In one embodiment, the cleansing composition can include one or more polymers. The one or more polymers can provide many benefits, for example, structure the cleansing composition; modify the rheology of the cleansing composition; and improve lather, skin feel, and/or deposition of benefit agents or antimicrobial agents included in the cleansing composition and the like. In one embodiment, the one or more polymers can be hydrophobically modified polymers or other suitable structuring polymers, cationic polymers, deposition polymers, and the like.

For example, in one embodiment, the cleansing composition can optionally include from about 0.01% to about 10%, from about 0.1% to about 8%, or from about 0.1% to about 5%, by weight of the cleansing composition, of a hydrophobically modified polymer. Suitable hydrophobically modified polymers can include Acrylates/Vinyl Isodecanoate Crosspolymer (Stabylen 30 from 3V), Acrylates/C10-30 Alkyl Acrylate Crosspolymer (Pemulen TR1 and TR2), Ammonium Acryloyldimethyltaurate/Beheneth-25 Methacrylate Crosspolymer (Aristoflex HMB from Clamant), Acrylates/Beheneth-25 Methacrylate Copolymer (Aculyn 28 from Rohm and Haas); Acrylates/Steareth-20 Methacrylate Copolymer (Aculyn 22 from Rohm and Haas), PEG-150/Decyl Alcohol/SMDI Copolymer (Aculyn 44 from Rohm and Haas), PEG-150 Distearate (Aculyn 60 from Rohm and Haas), Acrylates/Steareth-20 Methacrylate Crosspolymer (Aculyn 88 from Rohm and Haas), Aqupec SER-150 (acrylates/C10-30 alkyl acrylates crosspolymer) comprising about C18 (stearyl) side chains and about 0.4% hydrophobic modification (HM), Aqupec HV-701EDR which comprises C8 (octyl) side chains and about 3.5% HM., Stabylen 30 (from 3V Sigma S.p.A), and Carbopol Aqua SF-1 (crosslinked acrylates copolymer) having average 4.5 carbon alkyl side chains and more than 50% HM, or combinations thereof.

The cleansing composition can also optionally include cationic polymers. Cationic polymers can improve the lathering and skin feel benefits of the cleansing composition during and after use. If present, the cleansing composition can include from about 0.001% to about 10%, from about 0.01% to about 5%, or from about 0.05% to about 1%, by weight of the composition, of a cationic polymer. Suitable cationic polymers for use in the cleansing composition disclosed herein can include, but are not limited to, cationic polysaccharides; cationic copolymers of saccharides and synthetic cationic monomers; cationic polyalkylene imines; cationic ethoxy polyalkylene imines; cationic poly[N-[3-(dimethylammonio)propyl]-N'[3-(ethyleneoxyethylene dimethyl ammonio)propyl]urea dichloride]; or combinations thereof. Suitable cationic polymers can include polymers having a quaternary ammonium or substituted ammonium ion.

In certain embodiments, the cleansing composition can optionally include from about 0.001% to about 10%, from about 0.01% to about 5%, or from about 0.05% to about 1%, by weight of the cleansing composition, of a deposition polymer. Suitable deposition polymers can include cationic hydroxyethyl cellulosic polymers (polyquaternium 10, UCARE polymer JR400, LR400, JR30M, KG30M), cationic guar polymers (JAGUAR® from Rhodia (Jaguar C13S, Jaguar C14S, Jaguar C-17, Hi-Care 1000, Jaguar Excel, Jaguar CHT), and N-HANCE® polymers from Aqualon (N-Hance 3000, N-Hance 3196, N-Hance 3198, N-Hance 3205, N-Hance 3215, N-Hance 3269, N-Hance 3270), synthetic acrylamide polymer (polyquaternium 76), and combinations thereof.

The cleansing composition can also optionally include from about 0.01% to about 15%, from about 0.1% to about 10%, or from about 1% to about 5%, by weight of the cleansing composition, of a gum. Suitable gums for use in the cleansing composition disclosed herein can include carrageenan, gelatin, xanthan, gellan, pectin, guar, alginate, wellan, pullulan, and combinations thereof.

In one embodiment, the cleansing composition can include from about 5% to about 50%, from about 10% to about 40%, or from about 20% to about 30%, by weight of the cleansing composition, of a block copolymer. Examples of a block copolymer can include, for example, an F87, F88, F98, F108, or F127 Pluronic®, or a combination thereof.

The cleansing composition can optionally include inorganic salts. In one embodiment, the inorganic salts can help bind water in the cleansing composition thereby preventing water loss by evaporation or other means. The cleansing composition can optionally include from about 0.01% to about 15%, from about 1% to about 12%, or from about 2.5% to about 10.5%, by weight of the composition, of an inorganic salt. Suitable inorganic salts can include magnesium nitrate, trimagnesium phosphate, calcium chloride, sodium carbonate, sodium aluminum sulfate, disodium phosphate, sodium polymetaphosphate, sodium magnesium succinate, sodium tripolyphosphate, aluminum sulfate, aluminum chloride, aluminum chlorohydrate, aluminum-zirconium trichlorohydrate, aluminum-zirconium trichlorohydrate glycine complex, zinc sulfate, zinc carbonate, ammonium chloride, ammonium phosphate, calcium acetate, calcium nitrate, calcium phosphate, calcium sulfate, ferric sulfate, magnesium chloride, magnesium sulfate, and combinations thereof.

The cleansing composition can optionally further include one or more antibacterial agents that can serve to further enhance antimicrobial effectiveness of the cleansing compositions. If present, the cleansing composition can include from about 0.001% to about 5%, from about 0.01% to about 2%, from about 0.1% to about 1%, or from about 0.2% to about 0.5%, by weight of the cleansing composition, of the one or more antimicrobial agents. Examples of antibacterial agents can include the carbanilides, for example, triclocarban (also known as trichlorocarbanilide), triclosan, a halogenated diphenylether available as DP-300 from Ciba-Geigy, hexachlorophene, 3,4,5-tribromosalicylanilide, and salts of 2-pyridinethiol-1-oxide, salicylic acid and other organic acids, and a pyrithione or a polyvalent metal salt of pyrithione such as a zinc pyrithione.

The cleansing composition can optionally further include a benefit agent. Suitable benefit agents include, for example, petrolatum, mineral oil, soy bean oil, paraffin, polyethylene, polybutene, polydecene, dimethicone, alkyl siloxanes, cyclomethicones, lanolin, sucrose polyesters, or combinations thereof.

III. Methods of Manufacture

Personal care articles can be manufactured by adding the cleansing composition to an appropriate substrate via a conventional method which may include, but is not limited to, spraying, slot coating, molding such as rotary molding, extrusion, injection, feeding from a hopper and cutting such as by wire cutting, and roll transfer (e.g., pressure roll). A second substrate can then be placed on the first substrate over at least part of the cleansing composition. The personal care articles may also be manufactured by a hot melt method as discussed in the application titled "Personal Cleansing Articles Comprising Substrates and Cleansing Compositions and Methods of Making the Same" filed on even date herewith and is incorporated herein by reference. The substrates can be sealed together by a conventional sealing method which may include, but is not limited to, heat, pressure, glue, ultrasound, etc. Optional manufacturing steps may include calendaring to flatten the article as well as drying.

IV. Methods of Use

A method of cleansing the skin and/or hair with a personal cleansing article can include wetting with water a reusable personal cleansing article and contacting the skin or hair with the wetted personal cleansing article.

The personal care articles can be intended to be wetted with water prior to use. The personal care article can be wetted, for example, by immersion in water or by placing the personal cleansing article under a stream of water. In one embodiment, lather can be generated from the personal care article by mechanically agitating and/or deforming the personal cleansing article either prior to or during contact of the personal cleansing article with the skin and/or hair. The resulting lather can be useful for cleansing the skin and/or hair. During a cleansing process and subsequent rinsing with water, any therapeutic or aesthetic benefit agents can be deposited onto the skin and/or hair. Deposition of the therapeutic or aesthetic benefit agents can be enhanced by physical contact of the substrate with the skin and/or hair as well by the inclusion of one or more deposition aids.

V. Procedures

The personal care article, compositions, and substrates can include and/or exhibit specific physical properties as defined by the water flux rate test, the consumption rate test, the substrate and article tensile test, the dissolution rate test, an oscillatory rheology test, and/or the compliance test, which are described below.

A. Water Flux Rate Test

The water flux rate test can measure water permeability of a substrate. Without intending to be limited by theory, water permeability can be a principal determinant of surfactant longevity in a lathering substrate that is used in a presence of water, especially running water. When a surfactant can be present, it can be desirable for the surfactant to lather quickly and profusely, yet be fully depleted at an intended time to signal disposability of a used substrate. If water flux rate is too low, e.g. zero or near zero, insufficient wetting of the surfactant contained in the substrate can cause lather to start too slowly. On the other hand, if water flux rate is too high, surfactant can be too readily flushed from the substrate, and the composition will not last long enough.

To measure the water flux rate, with tape or rubber bands, affix a substrate to the bottom of a plastic funnel with the following measurements: a 24 mm inner diameter (i.d.) at an exit, a 145 mm i.d. at the top, 135 mm height (from the top to an onset of a neck), a 20 mm length neck, and a total volume of about 600 mL. Apply sufficient tension to the substrate to ensure the substrate is completely flat, and no more. Affix tape and rubber bands as close as possible to the exit of the funnel to keep backflow from occurring under water pressure. Next, clamp the funnel in a ring stand over a sink. Measure out 600 mL of water at room temperature in a graduated cylinder. Then, with one hand blocking the funnel exit, pushing against the test substrate, quickly pour the water into the funnel. Once the funnel is completely filled, remove the hand and measure drainage time for the water to evacuate the funnel to a nearest tenth of a second. Stop timing when the water reaches a junction of the neck and a sloped portion of the funnel. Repeat this process 5 times per test substrate and average the measurements for each substrate.

Substrates which exhibit long drainage times (about 10 minutes or longer) can be tested by weighing the water drained in a set time period (e.g. 5 minutes) with a funnel full of water and then algebraically determining the flux time for 600 mL of water. Next, measure the water flux rate in the opposite substrate direction (unless the substrate is the same in both directions), and average both results. For substrates with high surface tension against water and small pores (i.e., flow is observed to increase significantly with small amount of surfactant added), add a small but sufficient amount of wetting agent to the water (e.g., Dawn®™ dish liquid), to at least a critical micelle concentration, so that water flows through the substrate unimpeded by wetting forces prior to the test. The water flux rate is expressed in cm$^3$/cm$^2$/s according to the following equation: Water flux rate=(600 g water)×(1 cm$^3$/g)/((1.2 cm)$^2$×(average time in seconds)).

B. Consumption Rate Test

To measure the Consumption Rate of a personal care article or composition, use a rotary tumbler (Lortone, Inc., Seattle, Wash., USA model 33B or equivalent) with 4 in. diameter by 4 in. deep cylindrical rubber housing having 825 cc internal volume. The housing revolves on the tumbler at 43 rpm. Obtain a supply of tap water at about 7.5 grains water hardness and conductivity between 100 to not more than 400 microSemens per centimeter (0/cm) and heat in a reservoir beaker to 45° C. Maintain the water supply at the target temperature within 1 degree for the test duration. Add 200.0 gm water from the reservoir to the housing. Weigh an article or composition to obtain the initial weight, and add the article or composition to the housing. Seal the housing with its accompanying watertight lid and place the sealed housing onto the rotary tumbler for exactly 3 minutes. Remove the housing, remove the housing lid, and retrieve the article or composition. Stir the remaining water in the housing for a few seconds and measure its conductivity and temperature using a Mettler Toledo Seven multimeter with InLab 740 probe or equivalent. Dry the article or composition surface by pressing, not rubbing, using paper towels with light hand pressure for about 30 seconds, until it is dry to the touch and transfers no more visible water to a dry paper towel using the same pressure at any point on its surface or edges. If the article or composition transfers partially dissolved or dissolving components in addition to liquid water, for example if the composition is a conventional bar soap it may transfer paste-like material, the transferred components are to be removed and the article or composition is considered dry when visible transfer is no longer evident. Weigh the Article or Composition.

Empty and rinse the housing in hot tap water and dry it to complete 1 cycle. Repeat the cycle with the same article 4 more times for a total of 5 cycles. Measure the conductivity of the water reservoir at 30° C., 35° C., 40° C., and 45° C. Using a new article of the same composition, prepare a 1% solution by removing 1.00 grams of its dissolvable chemical composition and adding it to 99.00 grams of water from the reservoir. Dissolve the chemical composition completely, using agitation and heat as necessary. Measure conductivity of the 1% solution at the same 4 temperatures. Prepare a 2% solution in the same way (2.00 grams composition in 98.00 grams water), and measure its conductivity at the same 4 temperatures. Regress the conductivity vs. temperature results for each solution (0%, 1%, and 2%) and obtain the algebraic expressions for each.

For each conductivity-temperature datum for the water in the housing obtained during the each cycle, calculate the regressed conductivity for the 0%, 1% and 2% solutions at the temperature measured by the InLab 470 probe for each cycle. Execute a second set of linear regressions for each temperature obtained in the cycles using the solution concentrations (0%, 1% and 2%) as the y (output) and the regressed conductivity values as x (input). Use this second regression at each temperature obtained in each cycle with its paired conductivity value obtained as the input value for x to obtain y, which is the amount of solids of the article dissolved for each cycle. Add the dissolved solids for the 5 cycles and divide by 5 to obtain the Average Dissolved Solids. Multiply the value by 1.67 to obtain the consumption rate of the article which is based on the relationship between this method and consumption during use of articles in an average ad lib shower by consumers.

C. Substrate and Article Tensile Test

To measure the rigidity of a substrate and/or article, use a Texture Analyzer TA-XT2i (Texture Technologies Corp, NY, USA) tensile tester equipped with at least 5 kg load cell and adjustable upper and lower grips at ambient conditions. Adjust a gauge length of an instrument (grip to grip closest distance) to 50 mm. Cut 1 inch wide, long strips of the personal cleansing article or water insoluble substrate using a precision cutter in a machine direction (MD). (Note: Properties of an article can be measured by separating the cleansing composition from the substrates of the article by physical means and cutting 1 inch wide strips of the personal cleansing article with the cleansing composition removed.) If the strips are too short, adjust the gauge length of the instrument to accommodate the strips of the substrate, since the results are expressed in strain. Additionally, if the strips are too narrow, evaluate by normalizing results obtained to a 1 inch width arithmetically.

Affix the strips to grips in the instrument and program the instrument in tensile mode to pull at a rate of 5 mm/second and measure grams-force, using a 2.5 gram trigger to commence recording, for 20 seconds (100 mm). Next, record force at 10% strain in grams (5 mm) and divide the recorded force by 25.4 mm to express a stiffness value in units of grams per mm width (g/mm). Record peak force (grams) and divide the recorded peak force by width to generate the ultimate tensile strength in g/mm width of the article or substrate. For materials which exceed the capacity of a load cell, reduce the width of the strips or increase the load cell capacity to measure the stiffness and ultimate tensile strength.

D. Dissolution Rate Test

Obtain a straight walled glass beaker having an inside diameter (i.d.) of 63 mm and an inside height of 87 mm, (e.g. Pyrex 250 ml (No. 1000) which are widely available). Pour 150 grams of distilled water at ambient temperature (75° F.) into the beaker and add a Teflon® coated magnetic stir bar to the beaker. (Note: The stir bar can be nominally 1.5 inches long×⁵⁄₁₆ inches diameter, octagonally shaped as viewed from the end, and can have a ¹⁄₁₆ in. wide molded pivot ring around its center where the diameter can be about 0.35 in.) Examples of a suitable stir bar can include Spinbar® magnetic stir bars available from Sigma Aldrich Corp. worldwide including Milwaukee, Wis., USA and at www.sigmaaldrich.com.

Measure and record the water conductivity of the water using a conductivity meter, e.g., a Mettler-Toledo Seven-Multi meter with InLab740 probe. (Note: The conductivity of the water should be about 2 microSemens/cm (uS/cm) or less to indicate a low level of dissolved solids present.) Remove the conductivity probe from the water and place the beaker onto a digitally controlled laboratory stirrer, for example Ika® Werke RET Control-visc available, e.g., from DivTech Equipment Co, Cincinnati, Ohio, USA. Center the beaker on the stirrer and turn the stirrer on to obtain a constant rotation speed of 500 rpm to establish a vortex in the water which measures about 3 cm in depth from highest point of water at the beaker edge to the lowest point of air at the vortex center. Observe the vortex from above to ensure the beaker is centered and the magnetic stir bar is centered in the vortex. Weigh 1.0 grams of a composition pressed or formed together as a single unit and add it to the water near the beaker edge but not touching the beaker edge. Begin a timer and allow the water with composition to stir for 1 minute.

Turn off the stirrer. Insert the conductivity probe into the water in a location away from any undissolved material. Allow a measurement to stabilize for a few seconds and record conductivity. Turn the stirrer back on. Restart the timer as the digital readout passes 250 rpm. After an additional 1 minute has elapsed, turn off the stirrer and measure and record conductivity in the same manner as above. Turn the stirrer back on. Restart the timer as the digital readout passes 250 rpm. Repeat the process until a conductivity reading has been obtained every minute of stirring, for 5 minutes.

After taking a 5 minute conductivity reading, cap the beaker with a suitable watertight cover, e.g., plastic wrap. Shake the beaker vigorously for about 1 minute to dissolve remaining solids, using a vortex type agitator and/or mild heating in addition if necessary until all soluble components are observed dissolved by visible inspection. Cool the solution to less than 80° F. prior to the final measurement. Uncap the beaker, measure conductivity and record the value as a final conductivity.

Calculate the fractional dissolution ($f$) at each time point by the equation: $f$=(conductivity−water conductivity)/(final conductivity−water conductivity)

Calculate the dissolution half-life by fitting the fractional dissolution time series (6 points from 0 to 5 minutes) to a second order polynomial and calculate an interpolated or extrapolated result for a time at which a composition is half dissolved (i.e., f=0.5).

Dissolution half-life can be a measure of the propensity of a composition to resist solubilization by water. Bars of soap, for example, can have a dissolution half-life of 21.1 minutes (Ivory®™ Soap), exhibiting longevity and low consumption rate during use without a need for substrates as barriers to permeability. Liquid body wash can have a dissolution half-life of less than ½ minute and can be unsuitable as a composition for some articles.

E. Compliance Test

To measure the compliance of a composition and/or article, use a Texture Analyzer TA-XT2i (Texture Technologies Corp, NY, USA) equipped with at least a 5 kg load cell and a 0.75 inch ball probe at ambient conditions, with the probe zero point at an article or composition top surface using 0.5 gram-force to register a probe height, and a 2 gram-force to commence data collection for both force and distance. Measure a compressive force (kg) at a compression rate of 1 mm/sec over a depth of 5 mm, ensuring the composition and/or article form a flat surface over contact area with the ball probe, near the center of the article or composition. Repeat measurements as needed (e.g. at least 3 times) to obtain a representative average value. To determine the compliance of the composition and/or article divide the maximum observed force (kg) by the maximum compression depth (5 mm). When using a 5 kg load cell some samples may exceed capacity, in this case the maximum compression depth will be less than the set depth of 5 mm, specified in the procedure.

VI. Examples

The following examples further describe and demonstrate some embodiments within the scope of the present invention. In the following examples, all ingredients are listed at an active level. The examples are given solely for the purpose of illustration and are not to be construed as limitations of the personal care article or components thereof such as the composition or substrate, as many variations thereof are possible without departing from the spirit and scope disclosed herein.

A. Example Cleansing Compositions

Examples 1A-1C

Prepare representative cleansing compositions for a personal care article by combining each of the ingredients listed in Examples 1A-1C except the Sodium/Magnesium Silicate (clay) and mixing until homogeneous. Then, add the Sodium/Magnesium Silicate (clay) and speed mix using, for example, a speed mixer such as a Hauschild Engineering model DAV 400 FV, Germany, at 2500 rpm for 45 seconds until homogeneous.

|  | Ex. 1A | Ex. 1B | Ex. 1C |
|---|---|---|---|
| Sodium Laureth-1 Sulfate | 20.76 | 28.32 | 24.0 |
| [1]Cocoamidopropyl Betaine | 2.65 | 3.63 | 3.08 |
| Citric Acid | 0.63 | 0.86 | 0.73 |
| Preservatives | 0.24 | 0.24 | 0.20 |
| Perfume | 0.63 | 1.25 | 1.06 |
| Sodium/Magnesium Silicate (clay) | 35.0 | 45.0 | 45.0 |
| Glycerin, 99.7% USP | 25.0 | 0 | 0 |
| Petrolatum | 0 | 0 | 10.0 |
| Water | QS | QS | QS |
| Dissolution Half Life | 4.89 min. | — | — |

[1]Amphosol LB, Stepan Co, Northfield, IL, USA

Examples 2A-2J

Prepare representative cleansing compositions for a personal care article by combining each of ingredients listed in Examples 2A-2J, in a planetary Kitchen Aid mixer and stirring until homogeneous.

|  | Ex. 2A | Ex. 2B | Ex. 2C | Ex. 2D | Ex. 2E | Ex. 2F | Ex. 2G | Ex. 2H | Ex. 2I | Ex. 2J |
|---|---|---|---|---|---|---|---|---|---|---|
| [1]Sodium laureth-1 sulfate | 49 | 38.5 | 28 | 56.4 | 44.3 | 32.2 | 24.5 | 19.3 | 14 | 28.6 |
| Corn starch (raw) | 30 | 45 | 60 | 30 | 45 | 60 | 30 | 45 | 60 | 45 |
| Water | 21 | 16.5 | 12 | 13.6 | 10.7 | 7.8 | 45.5 | 35.2 | 26 | 26.4 |
| Dissolution Half Life/min. | 1.92 | 2.38 | 2.29 | 3.03 | 2.73 | 2.53 | 1.25 | 1.42 | 1.02 | — |

[1]added from 70% surfactant paste, all water derived from incoming materials

Example 3

Prepare a representative cleansing composition for a personal care article by combining each of the ingredients listed in Example 3 in a soap amalgamator to generate a composition, transfer the composition to an industrial 3-roll mill, and milling the composition thrice until the composition is paste-like with no lumps or particles.

|  | Ex. 3 |
| --- | --- |
| Vegetable Soap Base noodles (Palm, Coconut Oil) | 59.38 |
| Vegetable Glycerin, 99.7% USP | 39.37 |
| Perfume | 1.25 |
| Dissolution Half Life | 3.54 min. |

Example 4

Prepare a representative cleansing composition for a personal care article by combining pectin and glycerin and heating to 80° C. Add Sodium Trideceth-3 Sulfate and reheat the mixture to 80° C., then cool the mixture and speed mix using a Hauschild (Germany) model DAC 400 FVC Speedmixer at 2,000 rpm for 1 minute or until smooth.

|  | Ex. 4 |
| --- | --- |
| Pectin (dietary grapefruit) | 7.5 |
| Glycerin, 99.7% USP | 35.0 |
| Sodium Trideceth-3 Sulfate | 37.4 |
| Water | QS |

Examples 5A and 5B

Prepare a representative cleansing composition for a personal care article by combining each of ingredients listed in Examples 5A and 5B, respectively, and speed mix at 2,000 rpm for 1 minute.

|  | Ex. 5A | Ex. 5B |
| --- | --- | --- |
| Example 1B composition | 98.5 | 96.0 |
| [2]Zinc Pyrithione | 0.50 | 2.0 |
| Water | QS | QS |

[2]added from 48.9% active dispersion of Fine Particle Size Zinc Omadine (Arch Chemicals, USA)

Example 6

Prepare a representative cleansing composition for a personal care article by combining each of the ingredients listed in Example 6, heating to 85° C. until homogeneous and clear, pouring into a 1 cm deep mold, and cooling until hard and peelable from the mold in a layer.

|  | Ex. 6 |
| --- | --- |
| Sodium Laureth-1 sulfate | 10.1 |
| Lauryl amidopropylbetaine | 3.6 |
| Perfume | 0.5 |
| Preservatives, chelant, misc. | 1.0 |
| Gelatin | 7.3 |
| Glycerin, 99.7% USP | 37.0 |
| Water | QS |

Example 7

Prepare a representative cleansing composition for a personal care article by combining each of the ingredients listed in Example 7, heating to 85° C. until homogeneous and clear, pouring into a beaker, and cooling until hard. Scrape the hardened composition from the beaker into a container for storage or place into a substrate(s) or wrap to form a personal care article.

|  | Ex. 7 |
| --- | --- |
| Sodium Laureth-1 sulfate | 26.0 |
| Lauryl amidopropylbetaine | 3.3 |
| Perfume | 0.8 |
| Preservatives, chelant, misc. | 1.0 |
| Gelatin | 7.3 |
| Glycerin, 99.7% USP | 40.0 |
| Water | QS |

Example 8

Prepare a representative powdered cleansing composition for a personal cleansing article by combining each of the ingredients listed in Example 8, speed mixing the mixture at 2,000 rpm for 30 seconds to generate a free flowing powder with lumps that can be easily broken.

|  | Ex. 8 |
| --- | --- |
| Sodium Trideceth-2 sulfate | 32.5 |
| Sodium/Magnesium Silicate (clay) | 50.0 |
| Water | QS |

Example 9

Prepare a representative viscoelastic cleansing composition for a cleansing article by combining each of the ingredients listed in Example 9, adjusting the pH to 3.0-6.5 using sodium hydroxide and/or citric acid prior to addition of sodium/magnesium silicate, then add the sodium/magnesium silicate and speed mix the mixture at 2,000 rpm for 30 seconds until homogenous.

|  | Ex. 9 |
| --- | --- |
| Surfonic L24-9 | 5.47 |
| Linear Alkylbenzene Sulphonic Acid | 14.6 |
| Sodium Hydroxide | 4.6 |
| Citric Acid | 0.5 |
| Sodium/Magnesium Silicate (clay) | 41.1 |
| Water | QS |

Example 10

A representative skin and hair benefit composition for a cleansing article is prepared by making a 28.4% aqueous solution of Pluronic F127 by combining Pluronic F127 with water cooled to less than 5 degrees Celsius, combining each of the ingredients listed in Example 10, and speed mixing the mixture at 2,000 rpm for 30 seconds until homogenous.

|  | Ex. 10 |
| --- | --- |
| Pluronic F127 | 5.47 |
| Sodium Laureth-1 sulfate | 0.10 |
| Polyquaternium 76 | 0.25 |

|  | Ex. 10 |
| --- | --- |
| Polydimethicone DC-200, 10,000 cst | 7.5 |
| Water | QS |

Example 11

A representative cleansing composition can be prepared by making a 10% aqueous solution of Celvol 523 polyvinyl alcohol by combining Celvol with water heated to 50° C., combining the aqueous solution of Celvol 523, Sodium laureth-1 Sulfate and DC-200 and speed mixing the mixture at 2,000 rpm for 30 seconds until homogenous. Then, add sodium tetraborate to the mixture and speed mix for 15 seconds at 2000 rpm until homogeneous.

|  | Ex. 11 |
| --- | --- |
| Cevol 523 Polyvinyl alcohol | 5.47 |
| Sodium Laureth-1 sulfate | 0.0059 |
| Polydimethicone DC-200, 10,000 cst | 50.0 |
| Sodium tetraborate | 0.00083 |
| Water | QS |

Example 12

A representative cleansing composition can be prepared by combining each of the ingredients listed in Example 12 and speed mixing the mixture at 2,000 rpm for 30 seconds to generate a free flowing powder with lumps that can be easily broken.

|  | Ex. 12 |
| --- | --- |
| Farmal CS3757 | 79.20 |
| Aquapec SER W-150 | 4.95 |
| Sodium laureth-1 Sulfate | 10.40 |
| Perfume | 1.24 |
| Water | QS |

Example 13

Prepare a representative cleansing composition for a personal care article by combining each of the ingredients listed in Example 13 in a soap amalgamator to generate a composition, transfer the composition to an industrial 3-roll mill, and milling the composition thrice until the composition is paste-like with no lumps or particles.

|  | Ex. 13 |
| --- | --- |
| Jordapon-CI Granule, Powder or Prill | 39.15 |
| Cocoamidyl propyl betaine | 3.6 |
| Glycerin | 35.1 |
| PEG 90M | 0.10 |
| Perfume | 1.25 |
| Water | QS |

Example 14

Prepare a representative cleansing composition for a shave prep article by combining each of the ingredients listed in Example 14 in a soap amalgamator to generate a composition, transfer the composition to an industrial 3-roll mill, and milling the composition thrice until the composition is paste-like with no lumps or particles.

|  | Ex. 14 |
| --- | --- |
| Jordapon-CI Granule, Powder or Prill | 37.4 |
| Cocoamidyl propyl betaine | 6.0 |
| Glycerin | 35.1 |
| PEG 23M | 0.50 |
| Citric Acid | 0.15 |
| Perfume | 1.25 |
| Water | QS |

Example 15

Prepare a representative cleansing composition for a shave prep article by combining each of the ingredients listed in Example 15 in a soap amalgamator to generate a composition, transfer the composition to an industrial 3-roll mill, and milling the composition thrice until the composition is paste-like with no lumps or particles.

|  | Ex. 15 |
| --- | --- |
| Jordapon-CI Granule, Powder or Prill | 41.5 |
| Cocoamidyl propyl betaine | 6.0 |
| Glycerin | 31.3 |
| PEG 90M | 0.10 |
| Perfume | 1.0 |
| Water | QS |

Example 16

Prepare a representative cleansing composition for a shave prep article by combining each of the ingredients listed in Example 16 in a soap amalgamator to generate a composition, transfer the composition to an industrial 3-roll mill, and milling the composition thrice until the composition is paste-like with no lumps or particles.

|  | Ex. 16 |
| --- | --- |
| Jordapon-CI Granule, Powder or Prill | 55.4 |
| Glycerin | 35.0 |
| PEG 90M | 0.10 |
| Perfume | 1.25 |
| Water | QS |

Example 17

Prepare a representative cleansing composition for a shave prep article by combining each of the ingredients listed in Example 17 in a soap amalgamator to generate a composition, transfer the composition to an industrial 3-roll mill, and milling the composition thrice until the composition is paste-like with no lumps or particles.

|  | Ex. 17 |
| --- | --- |
| Jordapon-CI Granule, Powder or Prill | 25.8 |
| Glycerin | 19.8 |

-continued

| | Ex. 17 |
|---|---|
| Polyvinyl Alcohol (Celvol 523) | 1.5 |
| Water | QS |

Example 18

Prepare a representative cleansing composition for a shave prep article by combining each of the ingredients listed in Example 18 in a soap amalgamator to generate a composition, transfer the composition to an industrial 3-roll mill, and milling the composition thrice until the composition is paste-like with no lumps or particles.

| | Ex. 18 |
|---|---|
| Jordapon-CI Granule, Powder or Prill | 26.1 |
| Glycerin | 20 |
| Polyvinyl Alcohol (Celvol 523) | 5.0 |
| Perfume | 1.25 |
| Water | QS |

Comparative Article Example 1

Comparative example 1 is commercially available wrapped bar soap that includes the following ingredients: sodium palm kernelate, sodium palmitate, fragrance, water, disodium EDTA. This commercially available bar is made by Johnson & Johnson and distributed as Super Sudzer™ e-z grip Soap™ and includes an inner substrate and an exterior substrate of formed films wrapping the bar which weigh about 1.34 grams per article. The inner bar weighs 70 grams (5,200% of the substrate). The first substrate of the article has a Water Flux of 12.8 $cm^3/cm^2/s$. The article is not compliant.

Comparative Example 2

Comparative example 2 is a commercially available bar soap that includes the following ingredients: sodium tallowate, sodium palmate, water, sodium cocoate, sodium palm kernelate, sodium chloride, fragrance, coconut acid, palm kernel acid, tallow acid, palm acid, and tetrasodium EDTA. This commercially available bar is of Ivory™ soap made by The Procter & Gamble Company. This bar is not compliant.

B. Example Substrates

1. Formed Films

| Code | Material Description | Caliper and Basis Weight | Pore count/area; and diameter | Water Flux Rate $cc/cm^2/s$ | Air Permeability $m^3/m^2/s$ |
|---|---|---|---|---|---|
| F1 | Hydroapertured polyethylene film on 100 mesh screen, white (Tredegar, Inc.) | 166 microns, 24.5 gsm | $1,780/cm^2$ — | 6.2 | 58 |
| F2 | Vacuum formed polyethylene film, white (SSRIS-CPM, Tredegar, Inc.) | 560 microns, 24.5 gsm | $115/cm^2$ — | 33.8 | 295 |
| F3 | Vacuum formed polyethylene film, white 22 Hex (Tredegar, Inc.) | 560 microns, 24.4 gsm | $91/cm^2$ ~500 micron | — | 130 |
| F4 | Vacuum formed polyethylene film, blue 11.2 Hex (Tredegar, Inc.) | 935 microns, 29.4 gsm | $22.2/cm^2$ 1.1 mm | — | 145 |
| F5 | Vacuum formed polyethylene film, green (Tredegar, Inc.) | 670 microns, 36.0 gsm | $49/cm^2$ 0.9 mm | — | 220 |
| F6 | Vacuum formed polyethylene film, white (Tredegar, Inc.) | 33.5 gsm — | $12.6/cm^2$ 1 mm | — | — |
| F7 | Vacuum formed polyethylene film 40 Hex | 418 microns, 35.8 gsm | $285/cm^2$ — | 11.5 | 16.2 |

Caliper: ASTM D645
Air Permeability: ASTM D737

2. Fibrous Nonwovens

| Code | Material Description | Basis Weight | Water Flux Rate $cc/cm^2/s$ |
|---|---|---|---|
| N1 | Spunlaid hydroentangled 100% PP (Avgol Nonwovens, NC, USA) | 47 gsm | 6.0 |
| N2 | Carded, calendar bonded all bicomponent PP/PE fiber (Fiberweb Inc., TN, USA) | 32 gsm | 20.7 |
| N3 | Spunbond, overbonded 100% PP (Experimental nonwoven) | 37 gsm | 2.1 |
| N4 | Carded, through air bonded 30/30/40 PP/Bicomponent PP-PE/Rayon (calendar patterned) | 62 gsm | 2.8 |

3. Fibrous Nonwoven Battings

| Code | Material Description | Caliper; and Basis Weight | Water Permeability $cc/cm^2/s$ |
|---|---|---|---|
| B1 | Quilter's Fusible batting, low loft all polyester (Fairfield Processing, Danbury, CT, USA) | 2.50 mm, 160 gsm | 58.3 |

3. Fibrous Nonwoven Battings

| Code | Material Description | Caliper; and Basis Weight | Water Permeability cc/cm²/s |
|---|---|---|---|
| B2 | Quilter's Fusible batting, low loft all polyester, ½ thickness (peeled) | 1.21 mm, 80 gsm | 71.3 |
| B3 | PROEF 12-334 polyester-bicomponent fiber blend batting (Libeltex, Belgium) | 1.54 mm, 100 gsm | — |
| B4 | PROEF 12-370 dual layer PET/copet bico and PP fibers; bulk layer with standard PET/coPET bico trilobal fibers (Libeltex, Belgium) | 0.60 mm, 55 gsm | — |
| B5 | Dry Web T30 SC batting, hollow PET + bico PET/PE fiber blend, through air bonded (Libeltex, Belgium) | 0.41 mm, 35 gsm | — |
| B6 | PROEF 12-372 batting, coarse polyester and PE/PET bico fibers (Libeltex, Belgium) | 0.55 mm, 50 gsm | — |
| B7 | Dry Web T23W batting, coarse polyester and bico fiber mix (Libeltex, Belgium) | 0.56 mm, 50 gsm | — |

Caliper measured at 0.8 grams/mm²

Example and Comparative Personal Cleansing Articles

The following illustrate various combinations of the examples of cleansing compositions and substrates to generate example personal cleansing articles.

| Example Article | Top side contact substrate | Bottom side contact substrate | First and second non-contact substrates | Total weight of substrates/g | Size of Article | Cleansing Component | Weight of Cleansing Component (g) | Cleansing component expressed as % of total substrate |
|---|---|---|---|---|---|---|---|---|
| A1 | Example F6, cones: male side to exterior | F2, cones: male side to interior | None | 0.65 | 3 in. × 4 in. | Example 3 | 78.20 | 12,031 |
| A2 | Example F6, cones: male side to exterior | Example F2, cones: male side to interior | None | 0.68 | 3 in. × 4 in. | Example 2B | 78.80 | 11,588 |
| A3 | Example F6, cones: male side to exterior | Example F2, cones: male side to interior | Example F2, cones: male side to interior | 1.38 | 3 in. × 4 in. | Example 3 | 79.70 | 5,775 |
| A4 | Example F6, cones: male side to exterior | Example F2, cones: male side to interior | Example F2, cones: male side to interior | 1.38 | 3 in. × 4 in. | Example 2B | 79.50 | 5,761 |
| A5 | Example F6, cones: male side to exterior | Example F2, cones: male side to interior | Example F1, cones: male side to interior | 1.35 | 3 in. × 4 in. | Example 3 | 79.90 | 5,919 |
| A6 | Example F6, cones: male side to exterior | Example F2, cones: male side to interior | Example F1, cones: male side to interior | 1.19 | 3 in. × 4 in. | Example 2B | 79.90 | 6,714 |
| A7 | Example F6, cones: male side to exterior | Example F2, cones: male side to interior | Example B2 | 2.96 | 3 in. × 4 in. | Example 3 | 79.70 | 2,693 |
| A8 | Example F6, cones: male side to exterior | Example F2, cones: male side to interior | Example B2 | 2.70 | 3 in. × 4 in. | Example 2B | 79.90 | 2,959 |
| A9 | Example F6, cones: male side to exterior | Example F2, cones: male side to interior | Example N1 | 1.76 | 3 in. × 4 in. | Example 3 | 79.80 | 4,534 |
| A10 | Example F6, cones: male side to exterior | Example F2, cones: male side to interior | Example N1 | 1.82 | 3 in. × 4 in. | Example 2B | 79.80 | 4,385 |
| A11 | Example F6, cones: male side to exterior | Example F2, cones: male side to interior | Example N2 | 1.38 | 3 in. × 4 in. | Example 3 | 79.80 | 5,783 |
| A12 | Example F6, cones: male side to exterior | Example F2, cones: male side to interior | Example N2 | 1.33 | 3 in. × 4 in. | Example 2B | 79.70 | 5,992 |
| A13 | Example F6, cones: male side to exterior | Example F2, cones: male side to interior | Example N3 | 1.52 | 3 in. × 4 in. | Example 3 | 78.40 | 5,158 |
| A14 | Example F6, cones: male side to exterior | Example F2, cones: male side to interior | Example N3 | 1.56 | 3 in. × 4 in. | Example 2B | 79.80 | 5,115 |
| A15 | Example F6, cones: male side to exterior | Example F2, cones: male side to interior | Example N4 | 2.02 | 3 in. × 4 in. | Example 3 | 79.90 | 3,995 |
| A16 | Example F6, cones: male side to exterior | Example F2, cones: male side to interior | Example N4 | 1.83 | 3 in. × 4 in. | Example 2B | 79.80 | 4,361 |
| A17 | Example F6, cones: male side to exterior | Example F2, cones: male side to interior | Example F1, cones: male side to interior | 1.35 | 3 in. × 4 in. | Example 1A | 81.24 | 6,018 |

-continued

| Example Article | Top side contact substrate | Bottom side contact substrate | First and second non-contact substrates | Total weight of substrates/g | Size of Article | Cleansing Component | Weight of Cleansing Component (g) | Cleansing component expressed as % of total substrate |
|---|---|---|---|---|---|---|---|---|
| A18 | Example F6, cones: male side to exterior | Example F2, cones: male side to interior | Example F1, cones: male side to interior | 1.35 | 3 in. × 4 in. | Example 4 | 79.38 | 5,880 |
| A19 | Example F2, cones: male side to interior | Example F6, cones: male side to exterior | Example F1, cones: male side to interior | 0.58 | 33 cm² | Example 2B | 80.00 | 13,793 |
| A20 | Example F2, cones: male side to interior | Example F6, cones: male side to exterior | Example F1, cones: male side to interior | 0.99 | 58 cm² | Example 2B | 80.00 | 8,081 |
| A21 | Example F2, cones: male side to interior | Example F6, cones: male side to exterior | Example F1, cones: male side to interior | 1.83 | 105 cm² | Example 2B | 80.00 | 4,372 |
| A22 | Example F2, cones: male side to interior | Example F6, cones: male side to exterior plus one interposing layer Ex. B2 | Example F1, cones: male side to interior | 2.14 | 84 cm² | Example 2B | 80.00 | 3,738 |

Other Example Articles Include:

Example Article A23—The composition in example 9 can be incorporated into an article including the formed film F1 as both the first and second substrate adjacent to the composition and sealed to form a chamber around the composition; and the formed film F2 as both the first and second water insoluble substrates which at least partially encase the first and second substrates and the composition.

Example Article A24—The composition in example 12 can be incorporated into a cleansing article comprising the following insoluble films; Fibrous nonwoven N3 as the interior substrates which surround the composition, Formed film F2 can be the bottom exterior substrate, and the top exterior substrate of the cleansing article can be an 84 gsm woven nylon mesh where the nylon fibers can be 10 micron in diameter. In this embodiment, 25% of the water insoluble substrate materials are formed films.

Lather and Consumption Properties Associated with the Example Articles

| Example Article | Water Flux of Interior substrates (cm³/cm²/s) | Consumption Rate g/use |
|---|---|---|
| A1 | NA (no interior layer) | 2.05 |
| A2 | NA (no interior layer) | 3.50 |
| A3 | 30.2 | 1.17 |
| A4 | 30.2 | 3.62 |
| A5 | 6 | 1.02 |
| A6 | 6 | 0.52 |
| A7 | 71.3 | 2.04 |
| A8 | 71.3 | 4.46 |
| A9 | 6 | 1.46 |
| A10 | 6 | 2.97 |
| A11 | 20.3 | 2.57 |
| A12 | 20.3 | 3.12 |
| A13 | 2.1 | 1.58 |
| A14 | 2.1 | 2.34 |
| A15 | 2.8 | 1.58 |
| A16 | 2.8 | 3.00 |
| A17 | 4 | 1.83 |
| A18 | 4 | 1.13 |
| A19 | 6.2 | 1.90 |
| A20 | 6.2 | 5.00 |
| A21 | 6.2 | 6.60 |
| A22 | 6.2 | 5.60 |
| A23 | 6.2 | 1.91 |
| Comparative 1 | 12.8 | 1.75 |
| Comparative 2 | NA | 2.20 |

Tensile Test Properties Associated with the Example Articles or Substrates

| Examples | Composite articles - 2 exterior and 2 interior sides | | | | Stiffness g/mm | Ultimate Tensile Strength g/mm |
|---|---|---|---|---|---|---|
| | Exterior 1 | Interior A | Interior B | Exterior 2 | | |
| A5, A6, A17, A18 | Formed Film F2 | Formed Film F1 | Formed Film F1 | Formed Film F6 | 26.0 | 89.4 |
| A3, A4 | Formed Film F2 | Formed Film F2 | Formed Film F2 | Formed Film F6 | 28.5 | 102.7 |
| A13, A14 | Formed Film F2 | Fibrous Nonwoven N3 | Fibrous Nonwoven N3 | Formed Film F6 | 159.6 | 517.2 |
| A9, A10 | Formed Film F2 | Fibrous Nonwoven N1 | Fibrous Nonwoven N1 | Formed Film F6 | 103.2 | 563.2 |
| A7, A8 | Formed Film F2 | Batting B2 | Batting B2 | Formed Film F6 | 20.1 | 90.3 |
| A15, A16 | Formed Film F2 | Fibrous Nonwoven N4 | Fibrous Nonwoven N4 | Formed Film F6 | 121.3 | 262.2 |
| A11, A12 | Formed Film F2 | Fibrousn Nonwoven N2 | Fibrousn Nonwoven N2 | Formed Film F6 | 86.5 | 219.0 |
| Materials - single layers | | | | | | |
| | Formed Film F2 | | | | 7.0 | 33.8 |
| | Fibrous Nonwoven N3 | | | | 141.9 | 257.7 |

| | Composite articles - 2 exterior and 2 interior sides | | | Stiffness | Ultimate Tensile Strength |
|---|---|---|---|---|---|
| Examples | Exterior 1 | Interior A | Interior B | Exterior 2 | g/mm | g/mm |
| | | | Fibrousn Nonwoven N2 | | 23.5 | 60.2 |
| | | | Fibrous Nonwoven N1 | | 62.0 | 240.5 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compliant personal cleansing article, comprising:
   a) cleansing composition, comprising a rheology modifier and from about 10% to about 70%, by weight of the composition, of a synthetic surfactant; and
   b) a water penetrable first substrate surrounding the composition; wherein the article has a compliance of about 1.50 kg/mm or less.

2. The compliant personal cleansing article of claim 1, wherein the water penetrable substrate is a formed film.

3. The compliant personal cleansing article of claim 2, wherein the formed film has a basis weight of about 10 g/m$^2$ to about 100 g/m$^2$.

4. The compliant personal cleansing article of claim 1, wherein the article has a compliance value after 2 simulated uses of about 0.01 kg/mm to about 1.5 kg/mm.

5. The compliant personal cleansing article of claim 1, wherein the rheology modifier comprises clay, starch, a polymer, or a combination thereof.

6. The compliant personal cleansing article of claim 1, wherein the composition has a consumption rate of about 3.5 to about 10 gm/use.

7. The compliant personal cleansing article of claim 1, where the composition is about 4000 wt. % or more, by weight of the substrate.

8. The compliant personal cleansing article of claim 1, wherein the article has a compliance of about 0.03 to about 1.5 kg/mm.

9. The compliant personal cleansing article of claim 1, wherein the synthetic surfactant comprises a linear alkyl sulfate, a branched alkyl sulfate, linear alkyl ether sulfates, branched alkyl ether sulfates, linear alkyl sulfonates, branched alkyl sulfonates, linear alkyl ether sulfonates, branched alkyl ether sulfonates, or a combination thereof.

10. The compliant personal cleansing article of claim 1, wherein the synthetic surfactant comprises an alkyl glucoside, alkyl polyglucoside, polyhydroxy fatty acid amide, alkoxylated fatty acid ester, sucrose ester, amine oxide, or mixtures thereof.

11. The compliant personal cleansing article of claim 1, wherein the synthetic surfactant comprises sodium cocoyl isethionate.

12. The compliant personal cleansing article of claim 1, wherein the cleansing composition has about 1 gram or more of the synthetic surfactant, by weight of the substrate.

13. The compliant personal cleansing article of claim 1, wherein the cleansing composition has about 5 grams or more of the synthetic surfactant, by weight of the substrate.

14. The compliant personal cleansing article of claim 1, wherein the cleansing composition further comprises an antibacterial agent.

15. The compliant personal cleansing article of claim 1, wherein the antibacterial agent comprises zinc pyrithione.

16. The personal cleansing article of claim 1, wherein the synthetic surfactant comprises isethionate, cocoamide monoethanolamine, cocoamidopropyl betaine, decyl glucoside, lauryl glucoside, an alkyl sufate, or a combination thereof.

17. The personal cleansing article of claim 1, wherein the composition is a soft solid.

18. The personal cleansing article of claim 1, wherein the water penetrable substrate surrounds the personal cleansing composition.

19. The personal care article of claim 1, wherein the article is reusable.

* * * * *